(12) United States Patent
Yamada et al.

(10) Patent No.: US 12,004,493 B2
(45) Date of Patent: Jun. 11, 2024

(54) LATE-ONSET ALZHEIMER'S DISEASE ANIMAL MODEL AND USES THEREOF

(71) Applicant: The Board of Regents of the University of Oklahoma, Norman, OK (US)

(72) Inventors: Hiroshi Yamada, Edmond, OK (US); Chinthalapally Rao, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 1191 days.

(21) Appl. No.: 16/429,978

(22) Filed: Jun. 3, 2019

(65) Prior Publication Data

US 2019/0387723 A1    Dec. 26, 2019

Related U.S. Application Data

(60) Provisional application No. 62/680,114, filed on Jun. 4, 2018.

(51) Int. Cl.
*A01K 67/027* (2006.01)
*A01K 67/0276* (2024.01)
*G01N 33/50* (2006.01)

(52) U.S. Cl.
CPC ..... *A01K 67/0276* (2013.01); *G01N 33/5088* (2013.01); *A01K 2217/20* (2013.01); *A01K 2227/105* (2013.01); *A01K 2267/0312* (2013.01)

(58) Field of Classification Search
CPC .................................................. A01K 67/0276
See application file for complete search history.

(56) References Cited

PUBLICATIONS

Yamada et al. (2015, Carcinogenesis, vol. 36(4), pp. 429-440) (Year: 2015).*
Rao et al. (2016, Cancer Res., vol. 76(3), pp. 630-642) (Year: 2016).*
Rao et al. (2018, Aging Cell, e12797, pp. 1-11) (Year: 2018).*
Rao et al. (2018, Cell Cycle, vol. 17(19-20), vol. 2321-2334) (Year: 2018).*
Sanchez-Varo et al., 2022, Int. J. Mol. Sci., vol. 23, pp. 1-46 (Year: 2022).*
Rabinovici et al., 2019, Continuum, vol. 25 (1, Dementia), pp. 14-33 (Year: 2019).*

* cited by examiner

*Primary Examiner* — Anoop K Singh
*Assistant Examiner* — David A Montanari
(74) *Attorney, Agent, or Firm* — Hall Estill Law Firm

(57) ABSTRACT

An animal model (e.g., mouse) and method of use, and cell culture assay method, for characterizing or screening a test compound for its effect on late onset Alzheimer's disease (LOAD). The test compound may be used as a therapeutic agent for treatment of Alzheimer's disease (AD). The AD animal model may be haploinsufficient for Shugoshin 1 (Sgo1) gene, or may comprise a genetic modification enabling modulation of Sgo1 expression in the brain of the animal when exposed to an Sgo1 expression-modulating compound, such as tamoxifen. After the test compound is administered to the animal model, the presence or amount of an AD biomarker is assessed or measured.

1 Claim, 28 Drawing Sheets

Data Summary ($P<0.05$, $N=5$)

Antioxidant panel [49 proteins]
  wt vs. Sgo1 24m increase   7 Hspd1 Hspa1a Hspa5 Hspa9 Txnrd1 Pkm2 Tkt
  wt vs. Sgo1 24m decrease   1 Phb2
  wt vs. Sgo1 12m  increase   1 Phb
  Sgo1 vs. Sgo1 24m increase   3 Gstm1 Prdx6 Tkt
  Sgo1 vs. Sgo1 24m decrease  2 Nnt Phb2

Mitochondria/Krebs cycle/energy metabolism panel [47 proteins]
  wt vs Sgo1 24m increase   14 Hspd1 Gpi Aco2 Fh1 Idh1 Idh2 Sdha Sucla2 Etfdh
                                Ndufv1 Ckmt1 Clpp Clpx Tufm
  wt vs. wt    24m increase   1 Sdhc
  wt vs. wt    24m increase   1 Rhot1
  wt vs. Sgo1   12m increase   1 Pdk1
  Sgo1 vs. Sgo1 24m increase   3 Aco2 Idh1 Idh2

Beta-oxidation/peroxisome panel   [37 proteins]
  wt vs. Sgo1   24m increase   3 Hspd1 Acaa2 Hadha
  wt vs. wt     24m increase   1 Hmgcs
  Sgo1 vs. Sgo1  24m  increase  1 Cat
  Sgo1 vs. Sgo1  24m decrease  1 Fabp3

FIG. 24

LATE-ONSET ALZHEIMER'S DISEASE ANIMAL MODEL AND USES THEREOF

CROSS-REFERENCE TO RELATED APPLICATIONS

This application claims priority to U.S. Provisional Application No. 62/680,114, filed on Jun. 4, 2018, which is expressly incorporated herein by reference in its entirety.

STATEMENT REGARDING FEDERALLY-SPONSORED RESEARCH OR DEVELOPMENT

This invention was made with government support under Contract Numbers. CA094962 and CA213987 awarded by the National Institutes of Health. The government has certain rights in the invention.

BACKGROUND

Alzheimer's disease (AD) is a leading cause of cognitive impairment and death among people older than 65. Five percent of AD develops early in life (familial/early-onset AD [EOAD]) facilitated by mutations in Amyloid Precursor Protein (APP), Presenilin 1, Tau, or APOE genes. The remaining 95% of human AD is late onset (LOAD). The exact cause of LOAD remains unclear, although inflammation, oxidative stress, cholesterol metabolism, glycation, and other environmental and lifestyle factors are recognized as aggravating factors.

Major pathological features of the human AD brain include plaques of polymerized amyloid-β, tangles of Tau proteins, and congophilic cerebral amyloid angiopathy. With insufficient knowledge of the cause, modeling LOAD in rodents has been problematic. Normally, mice do not develop AD, which has been interpreted as due to their shorter lifespan and sequence differences in APP and Tau. Various transgenic mouse models with modified APP, Tau, and others have been developed for EOAD. However, LOAD models are limited to apes and are practically non-existent in rodents. AD drugs developed with EOAD models have been explored for use as human LOAD therapy, under an assumption that drugs effective on EOAD would also be effective in treating LOAD. However, more than 98% of drugs tested in EOAD rodent models were ineffective in human LOAD patients in clinical trials, raising concerns about current drug targets and about the validity of the EOAD models for human LOAD.

Spontaneous late-onset Alzheimer's disease (LOAD) accounts for more than 95% of all human AD. Since mice do not normally develop AD, and since an understanding of the molecular processes leading to spontaneous LOAD has been insufficient to successfully model LOAD in mice, no mouse model for LOAD has been available. New methods of testing compounds for effectiveness against LOAD are needed and it is to meeting this need that the present disclosure is directed.

The following nonstandard abbreviations are used hereinbelow:

Aco2, Aconitase 2, mitochondrial; AD, Alzheimer's disease; APOE, Apolipoprotein E; APP, Amyloid Precursor Protein; amyloid-beta, amyloid-β, ARC/Arg3.1, Activity-regulated cytoskeleton-associated protein; BACE1, beta-secretase 1; COX-2, cyclooxygenase 2; EBF3, Early B Cell Factor 3; EOAD, early-onset Alzheimer's disease; Fabp3, fatty acid binding protein 3; Fh1, Fumarate Hydratase; Gpi, Glucose-6-phosphate isomerase; Hspd1, Heat Shock Protein Family D [Hsp60] Member 1; Idh1, Isocitrate Dehydrogenase [NADP(+)] 1, Cytosolic; Idh2, Isocitrate Dehydrogenase [NADP(+)] 2, Mitochondrial; IFN-gamma, IFN-γ, Interferon-gamma; IL1-beta, IL1-β, Interleukin1-beta; IL10, Interleukin 10; LOAD, late-onset Alzheimer's disease; mtUPR, mitochondrial unfolded protein response; NDUFV1, NADH:Ubiquinone Oxidoreductase Core Subunit V1; NFκB65, Nuclear Factor-kappaB 65kd subunit; nnt, Nicotinamide Nucleotide Transhydrogenase; Pdk1, Pyruvate Dehydrogenase Kinase 1; PKM2, Pyruvate kinase isozyme M2; prdx6, Perredoxin6; $PGE_2$, Prostaglandin $E_2$; Phb, Prohibitin; Phb2, Prohibitin2; p-MAPK, phosphor-mitogen activated protein kinase; PSEN1, Presenilin 1; Sgo1, Shugoshin 1; TNF-alpha, TNF-α, Tumor necrosis factor-alpha; phosphorylated tau protein (p-Tau); tau protein (Tau); Activity-regulated cytoskeleton-associated protein (ARC); phospho-Histone H3 (p-H3); proliferating cell nuclear antigen (PCNA); glial fibrillary acidic protein (GFAP); neuronal migration protein doublecortin (DCX); pro-melanin concentrating hormone (PMCH); D-amino acid oxidase (DAO); and Purkinje cell protein-2 (PCP2).

BRIEF DESCRIPTION OF THE DRAWINGS

FIG. 24 is a data summary for the group comparison analyses. Four groups of mice (12-month wild-type (wt), 12-month Sgo1$^{-/+}$, 24-month wt, and 24-month Sgo1$^{-/+}$) were compared for expressions of proteins of interest in the brain through a series of two-group comparisons (unpaired t-test). Multiple comparisons (e.g., two-way ANOVA) were not employed in the analysis, as appropriate correction method factoring both age-associated effects and strain-associated effects has not been determined. Proteins indicating statistically significant differences (P<0.05, N=5) between said groups are listed, and the numbers per comparison category are stated. Proteins showing an increase in 24-month Sgo1$^{-/+}$ compared with age-matched wt were most dominant in the number.

DETAILED DESCRIPTION

Figure 1A:
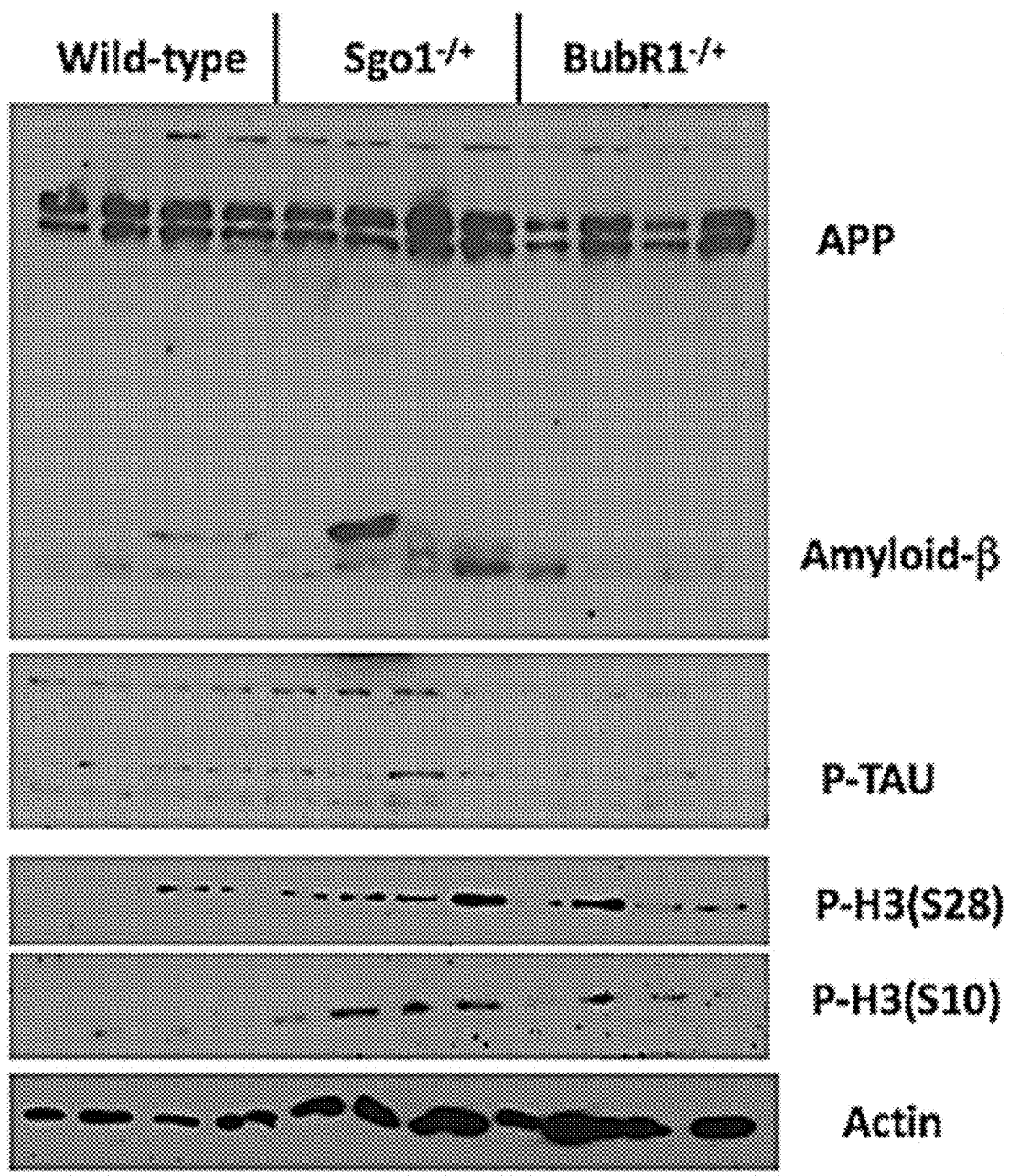
FIG. 1A shows that brains in haploinsufficient Shugoshin 1 ($Sgo1^{-/+}$) mice accumulated amyloid-β and mitotic marker phospho-Histone H3 (pH3) by the 24-month age equivalent to human old age. Immunoblots for APP/amyloid-β, phosphorylated-Tau, pH3 (Ser10), pH3 (Ser28), and actin (loading control) in wild-type (control), $Sgo1^{-/+}$, and $BubR1^{-/+}$ brain (cerebrum) extracts.

The present disclosure is directed, in at least certain embodiments, to animal models and method of their use, and cell culture assay methods, for screening a drug candidate for use as a therapeutic agent for treatment of late onset Alzheimer's disease (LOAD), and/or for characterizing a compound for its effect on progression of LOAD and/or for its effect on a biomarker of LOAD such as amyloid-β. The animal model may be haploinsufficient (−/+) for Shugoshin 1 (Sgo1) gene, or may comprise a genetic modification enabling modulation of Sgo1 expression in the brain of the animal upon exposure to an Sgo1 expression-modulating compound. When exposed to the Sgo1 expression-modulating compound, the brain cells of the animal (e.g., mouse) are induced to accumulate amyloid-β due to inhibition or reduction of Sgo1 expression. The cell culture of the assay may be obtained from primary brain cells cultured from an animal whose expression of Sgo1 gene has been genetically modified to enable modulation of Sgo1 expression in the brain of the animal when exposed to an Sgo1 expression-modulating compound, wherein the cells of the cell culture are induced to accumulate amyloid-β due to inhibition or reduction of Sgo1 expression.

Before further describing various embodiments of the present disclosure in more detail by way of exemplary description, examples, and results, it is to be understood that the embodiments of the present disclosure are not limited in application to the details as set forth in the following description. The embodiments of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the present disclosure has been described in terms of particular embodiments, it will be apparent to those of skill in the art that variations may be applied to the apparatus and/or methods and in the steps or in the sequence of steps of the methods described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the apparatus, methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

The term "animal" as used herein will be understood to refer to a warm blooded animal, particularly a mammal or bird. Non-limiting examples of non-human animals within the scope and meaning of this term, and which can be used in the methods and models described herein, include dogs, cats, rodents (e.g., rats, mice, guinea pigs, hampsters, gerbils), rabbits, pigs, chinchillas, horses, goats, cattle, sheep, llamas, zoo animals, and non-human primates such as Old and New World monkeys, and apes, including gorillas, chimpanzees, baboons, gibbons, bonobos, and orangutans.

"Treatment" refers to therapeutic or experimental treatments. "Prevention" refers to prophylactic treatment measures to stop a condition from occurring. The term "treating" refers to administering a composition to a subject for therapeutic or experimental purposes, and may result in an amelioration of the condition or disease.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as toxicity, irritation and allergic response) commensurate with a reasonable benefit/risk ratio when used in the manner of the inventive concepts.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Turning now to the models and and methods of the present disclosure, in at least one embodiment, the disclosure is directed to a modified Sgo1 animal model, such as a mouse model, which recapitulates the symptoms of Alzheimer's disease.

Existing animal AD models typically are early-onset AD (EOAD) models that rely on forcible expression of AD-associated protein(s), which may not recapitulate prerequisites for spontaneous LOAD. This limitation in AD modeling may contribute to the high failure rate of AD drugs in clinical trials. In the present work two mouse models of genomic instability in old-age brain pathology were studied. It was discovered that Shugoshin 1 (Sgo1) haploinsufficient (−/+) mice, a model of chromosome instability (CIN) with chromosomal and centrosomal cohesinopathy, spontaneously exhibited a major feature of AD pathology: amyloid-beta accumulation that co-localized with phosphorylated Tau, beta-secretase 1 (BACE), and mitotic marker phospho-Histone H3 (p-H3) in the brain. Another CIN model, spindle checkpoint-defective BubR1$^{-/+}$ haploinsufficient mice, did not exhibit the pathology at the same age, suggesting the prolonged mitosis-origin of the AD pathology. RNAseq identified ten differentially expressed genes, among which seven genes have indicated association with AD pathology or neuronal functions (e.g., ARC, EBF3). Thus, the Sgo1$^{-/+}$ mouse model recapitulates spontaneous LOAD pathology and represents a novel tool for investigating mechanisms of spontaneous progression of LOAD pathology, for early diagnosis markers, and for drug development.

Shugoshin 1 (Sgo1) protects cohesin proteins and centrosome integrity. Cohesins keep sister chromatids from prematurely separating during mitosis, thus ensuring mitotic fidelity. The Sgo1 haploinsufficient (−/+) mouse is a model of cohesinopathy and chromosome instability (CIN). The Sgo1$^{-/+}$ model has shown unique transcriptomic signatures at the tissue/organ level and cancer-proneness in certain organs including colon, lung and liver. In humans, the homolog SgoL1 is frequently mutated or abnormally expressed in cancers, affecting the mitotic process. Congenital mutations in human SgoL1 lead to chronic atrial and intestinal dysrhythmia (CAID) syndrome, affecting the heart and gut rhythm. However, whether the mutations affect AD is unknown. CAID syndrome is an extremely rare disease. The disease-associated SgoL1 missense mutation was found in less than 1% in public database. A likely reason for the rarity of CAID syndrome is that congenital mutation in human SgoL1 may not be compatible with early development. In mouse, Sgo1 is highly expressed in heart, gut, and CNS during early development, and Sgo1−/− (knockout) is embryonic lethal; strongly suggesting essential function of Sgo1 and SgoL1 during early development. The present work is the first to have linked Sgo1 and AD. As such, no study focusing on correlation between the CAID syndrome and AD has been performed thus far.

BubR1 is a mitotic spindle checkpoint component, BubR1$^{-/+}$ mice showed mitotic slippage in the cells and were colon cancer-prone, and BubR1$^{H/H}$ hypomorphic mice were identified as a model for premature aging. Neuronal cell division and axon growth were inhibited by siRNA-mediated BubR1 knockdown in the mouse brain. The above findings in BubR1 transgenic models led to a hypothesis that mitotic errors and CIN facilitate AD-like neurodegeneration. The present work, described in further detail below, thus investigated whether the Sgo1$^{-/+}$ or BubR1$^{-/+}$ haploinsufficient mouse could serve as a model for spontaneous LOAD progression.

Evidence provided herein demonstrates that the Sgo1$^{-/+}$ haploinsufficient mouse model displays AD-like brain pathology at an age equivalent to human old age. The model enables the testing of genetic interactions between known AD-associated genes (e.g., APOE, ARC) through simple breeding, as well as the influence from environmental, dietary, and other intervention or therapeutic measures. Genes directly or indirectly involved in AD pathology and its modulation (e.g., ARC, DAO, Ebf3, PPP1r17), along with genes that modulate neuronal function and/or behavior (e.g., PMCH, Shisa8, S1c6a5), were identified herein, strongly suggesting that Sgo1$^{-/+}$ haploinsufficiency affects the animal's cognitive functions and/or behavior at later ages.

Overall, the Sgo1$^{-/+}$ haploinsufficient mouse model represents the first genetically-defined spontaneous LOAD model, and thus enables the identification of drug candidates for treating LOAD, and investigation of the mechanisms of LOAD pathology development and in translational studies for intervention and therapy.

In at least certain embodiments, the mouse models of the present disclosure can be used to screen for and/or assess the effects of various drug candidates for use in treating AD. For example, animals can be treated with a drug candidate under a predetermined protocol for a predetermined duration (e.g., 1-6 months) prior to the endpoint of the experiment, then one or more biomarkers indicative of AD can be measured at the endpoint of the experiment (e.g., 18-24 months after birth). For example, the amyloid-β/APP ratio can be measured from brain extracts of test animals using immunoblot and compared to the amyloid-β/APP ratio measured from brain extracts of wild-type (control) animals and/or of untreated Sgo1−/+ animals. Amyloid-β is an established pathological biomarker for AD, and an increase in amyloid-βAPP ratio indicates accumulation of amyloid-β. Other AD biomarkers that can be measured include, but are not limited to, p-Tau, Tau, ARC, p-H3, cyclin B, PCNA, GFAP, DCX, PMCH, Gm20388, AA465934, Shisa8, Ebf3, DAO, S1c6a5, PPP1r17, and PCP2. Antibodies for detecting such biomarkers are commercially available.

Another major AD biomarker is cognitive and memory function and behavior integrity. With mice, video-based behavioral analyses can be performed on the test animals and compared to the wild type. In certain embodiments of the presently-disclosed models and assays, various behavioral actions or physical features can be assessed and/or tested such as, but not limited to motor coordination, motor learning, synaptic loss, neuron loss, axonal degeneration, gliosis, neurodegeneration, synaptic transmission, learning and memory behavior, differential glutamate response, long-term potentiation, modification and clearance of amyloid pathology, and/or brain volume.

In certain embodiments of the present disclosure, the AD mouse model is a brain-specific, inducible, Sgo1 knockout mouse strain. For example, cre-lox strains that carry brain/central nervous system-specific and an inducible promoter will be useful in generating strain(s) that knock out Sgo1 specifically in the brain in an inducible manner. For example, the AD mouse model may be a brain-specific, tamoxifen-inducible, Sgo1 knockout mouse strain. For example, the brain-specific, tamoxifen-inducible, Sgo1 knockout mouse strain may be a Sgo1-CRISPR-nestin-cre-lox mutant strain. Using the tamoxifen-inducible mouse system, tamoxifen is administered to the mutant mouse to knockout Sgo1 in the brain, the drug candidate (or other experimental test factor) is administered using a predetermined protocol, then at the end of the experiment, brains of the knockout mice are collected for measurement of the desired AD biomarkers (e.g., amyloid-β/APP ratio). In the Sgo1-CRISPR-nestin model used herein, the expression-modulating compound used for gene knockout is tamoxifen. However, cre-lox-host strains with promoters other than nestin can be used, wherein the modulator is a different chemical. Therefore, inducers ("expression modulators") other than tamoxifen can also be used in the models described herein, including but not limited to tetracycline and doxycycline.

Examples of cre-lox strains which can be used to cross with Sgo1-CRISPR strains to form tamoxifen-inducible cre-strains include, but are not limited to:

C57BL/6-Tg(Nes-cre/ERT2)KEisc/J (also known as: Nes-cre/ERT2);

Tg(S1c1a3-cre/ERT)1Nat/J (also known as: GLAST-CreER);

B6;C3-Tg(Wfs1-cre/ERT2)3Aibs/J (also known as: Wfs1-Tg3-CreERT2);

B6;129S6-Tg(Camk2a-cre/ERT2)1Aibs/J (also known as: CaMK2a-CreERT2);

B6.129(Cg)-Arctm1.1 (cre/ERT2)Luo/J (also known as: ArcCreER);

B6.Cg-Tg(Cspg4-cre/Esr1*)BAkik/J (also known as: NG2-CreERTM);
B6;129-Thtm1(cre/Esr1)Nat/J (also known as: TH-IRES-creER);
B6;FVB-Tg(Aldh1l1-cre/ERT2)1 Khakh/J (also known as: Aldh1l1-Cre/ERT2 BAC transgenic);
B6N.FVB-Tg(Aldh1l1-cre/ERT2)1Khakh/J (also known as: Aldh1l1-Cre/ERT2 BAC transgenic (C57BL/6N);
B6(Cg)-Pvalbtm1(cre/ERT2)Zjh/J (also known as: Pv-CreER);
B6.Cg-Nxph4tm1.1(cre/ERT2)Hze/J (also known as: Nxph4-2A-CreERT2-D);
B6.Cg-Penktm1.1(cre/ERT2)Hze/J (also known as: Penk-2A-CreERT2-D);
B6.Cg-Pvalbtm5.1(cre/folA)Hze/J (also known as: Pvalb-2A-dCre-D);
B6.Cg-Tg(Wfs1-cre/ERT2)2Aibs/J (also known as: Wfs1-Tg2-CreERT2);
B6;129S4-D1x1tm1(cre/ERT2)Zjh/J;
B6;CBA-Tg(Fgfr3-icre/ERT2)4-2Wdr/J;
C57BL/6N-Tg(Slc32a1-icre/ERT2)3Gloss/J;
Gad2tm1(cre/ERT2)Zjh/J (also known as: Gad2-CreER);
Nkx6-2tm1(cre/ERT2)Fsh/J; and
B6.Cg-Tg(Plp1-cre/ERT)3Pop/J.

A non-limiting example of a cre-lox strain which can be used to cross with Sgo1-CRISPR strains to form a trimethoprim-inducible cre-strain is:
B6;129S-Rasgrf2tm1(cre/folA)Hze/J (also known as: Rasgrf2-2A-dCre).

In one non-limiting embodiment, the brain-specific, tamoxifen-inducible, Sgo1 knockout mouse strain (Sgo1-CRISPR-nestin-cre-lox) can be made using the following method:
(1) Generate a Sgo1-frameshift strain with CRISPR-flox system, using CRISPR DNA Pronuclear (one cell embryo) Microinjection (using two gRNA+one ssOligo donor) to replace the wildtype exon 4 with the two-loxp-site flanking both LoxP sites and exon 4 of Sgo1. Cross-breed the floxed mice with Cre mice (with neuronal-specific promotor), so that the exon 4 (containing non 3n nucleotides) is removed and a frameshift is introduced afterwards, achieving the conditional knockout, providing at least two site specific germline transmitted (i.e. floxed) F1.
(2) Obtain C57BL/6-Tg(Nes-cre/ERT2)KEisc/J strain mice (Nes-cre strain) which expresses tamoxifen-inducible Cre recombinase under Nestin promoter in adult and developing mouse brain, including neuronal and glial cell precursors. The Nestin-Cre mice are readily available as repository live animals.
(3) Mate the Sgo1-CRISPR-flox strain mice with the C57BL/6-Tg(Nes-cre/ERT2)KEisc/J mice to generate F1 mice. The F1 are genotyped by PCR for Sgo1-CRISPR and Nes-cre. Among the F1, 50% carry both Sgo1-CRISPR and Nes-cre as hetero, and they are used for the next round of mating. The F1 mice are mated to generate F2 experimental mice Sgo1-CRISPR-Nestin-cre-lox. Among the F2 generation, 25% are estimated to carry desired genotype and they are designated as the experimental Sgo1-CRISPR-Nestin-cre-lox animals.

In alternate embodiments, in vitro AD test compound assays can be formulated from brain cells cultures from the experimental Sgo1-CRISPR-Nestin-animals (or other test animals described herein). For example, brain from Sgo1-CRISPR-nestin mice aged 3-6 months are minced and incubated in a culture medium to obtain primary cultured cells. The cells accumulate amyloid-β when an expression-modulating compound (inducer) is added to the culture medium and Sgo1-expression is shut down or reduced. A drug candidate for AD can be tested on the cultured cells by being added to the culture medium along with the expression-modulating compound tamoxifen. An efficacious drug candidate will cause a decrease in amyloid-β/APP ratio (indicating reduction of amyloid-β accumulation), compared with control cells not treated with the drug candidate. Such cultured cell-based in vitro assay can serve as a partial surrogate or substitute assay to the in vivo assay. In one non-limiting embodiment, the expression-modulating compound can be added once to initiate induction, and the drug candidate can be added one or more times during the test period before the amyloid-βAPP ratio (or other biomarker) is determined (e.g., after 2 days to 30 days). In one non-limiting embodiment, the test animal is grown normally for 10 to 12 months at which time Sgo1-expression is shut down or reduced ("knocked-out" or "knocked-down") by the addition of the expression-modulating compound (e.g., tamoxifen or other compound). The test compound is then provided to the test animal for a predetermined duration (e.g., 1, 2, 3, 4, 5, 6, 7, 8, 9, 10, 11, 12, 13, 14, 15, or 16 weeks or more), after which the animal is sacrificed and its brain is tested for one or more AD biomarkers.

The present disclosure will now be further discussed in terms of several specific, non-limiting, examples and embodiments. The examples described below, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of certain procedures as well as of the principles and conceptual aspects of the present disclosure.

Experimental Series I
Material and Methods
Animals

C57BL/6-based wild-type (WT), Sgo1$^{-/+}$, and BubR1$^{-/+}$ mice were bred and maintained in a pathogen-free rodent barrier facility without treatment for 24-25 months (an observational study). Surviving animals were euthanized and organs were collected. Animal numbers were: wild type (WT), N=14 (surviving out of 18); Sgo1$^{-/+}$, N=8 (out of 12); BubR1$^{-/+}$, N=15 (out of 21). All procedures were approved by the OUHSC Institutional Animal Care and Use Committee. Each brain was split in two hemispheres. One hemisphere was saved in 10% buffered formalin for immunofluorescence, and the other was stored at −80° C. after flash freezing in liquid nitrogen for immunoblots and/or RNAseq.

Immunoblots

Frozen brain samples (mouse cerebrum including cortex and hippocampus, excluding olfactory bulb, cerebellum, medulla) were extracted in extraction buffer and subjected to immunoblots following our standard protocol. Blots were quantified using ImageJ 1.43 software (NIH). Actin blots were used for loading control and normalization.

Immunofluorescence

Formalin-fixed brain hemispheres were embedded in paraffin and sectioned onto slides. After deparaffinization, antigen retrieval, sodium borohydride treatment, CuSO$_4$ treatment, and blocking, the slides were treated with primary antibodies for 16 hours, then with secondary fluorescent antibodies for 1 hour, followed by brief DAPI staining and sealing with antifade. Sodium borohydride and CuSO$_4$ were used to minimize autofluorescence by Shiff-base and by Lipofuscin, respectively.

We used multiple antibodies from different vendors, especially for APP and/or Amyloid-β to ensure accuracy of results. We used the following antibodies: anti-APP/Amyloid-β [Santa Cruz, sc-28385], anti-Amyloid-β (D54D2) [Cell Signaling Technologies (CST), 8243T], anti-Tau (Tau46) [CST, 4019T], anti-BACE (D10E5) [CST, 5606T], anti-APP/Amyloid-β (NAB228) [CST, 2450T], anti-phospho-Tau (PhosphoS262) [Antibodies-online/EnoGene, E011111], anti-phospho-HistoneH3 (S10) [CST, #9701], anti-phospho-HistoneH3 (S28) [CST, #9713], anti-Rabbit Cy5 [Jackson ImmunoResearch, #68551], and anti-mouse Alexa488 [Invitrogen, A11029]. The slides were observed with an Olympus microscope or a Leica microscope. We used the same image acquisition settings for all samples, so that visualized signal intensity would reflect the difference among samples (e.g., FIG. 1A, 1B).

Quantification of Immunofluorescence

In the experiment in FIGS. 3A-E and FIG. 6, immunofluorescence samples from brains of wild-type and Sgo1$^{-/+}$ mice (WT N=3, Sgo1$^{-/+}$N=3) were photographed (several sets per animal). In a pictured field, numbers of p-H3-positive cells and DAPI-positive cells were counted, and percentages of p-H3-positive cells among all DAPI-positive cells were calculated. A minimum of six fields were analyzed both for cortex and for hippocampus of wild-type and of Sgo1$^{-/+}$ mice.

RNAseq

Comparative RNA sequencing was performed. The total RNA was extracted from frozen brain samples (mouse cerebrum including cortex and hippocampus, excluding olfactory bulb, cerebellum, medulla). The RNA samples were submitted to the OUHSC Laboratory for Bioinformatics core facility for library construction and RNA sequencing with an Illumina MiSeq next-generation sequencer with each run generating approximately 30 million 2×150 bp paired end reads. The readouts were analyzed with Strand bioinformatics software (Strand-NGS, San Francisco, CA). Illumina MiSeq paired fastq files were aligned in Strand NGS software version 2.1 (www.strand-ngs.com) using mouse mm10 (UCSC) assembly. The December 2011 Mus musculus assembly (Genome Reference Consortium Mouse Build 38 [GCA_000001635.5]) was produced by the Mouse Genome Reference Consortium (http://genome.ucsc.edu/). Reads were normalized using DESeq. The normalized read counts were log-transformed and base-lined to the data set, resulting in normalized signal values. Differential gene expression of the normalized signal values between the control and experimental group was determined using a moderated t-test, P<0.05. The differentially expressed gene list was subsequently used for clustering and pathway analysis.

Statistical Analysis (RNAseq)

We used student's t-test to analyze the data. Statistical significance was evaluated by algorithms integral to the aforementioned software. FDR-adjusted P values of <0.05 were considered significant.

Data and Materials Availability

The RNAseq dataset was deposited to the NIH-GEO database.

Results

Figure 15:
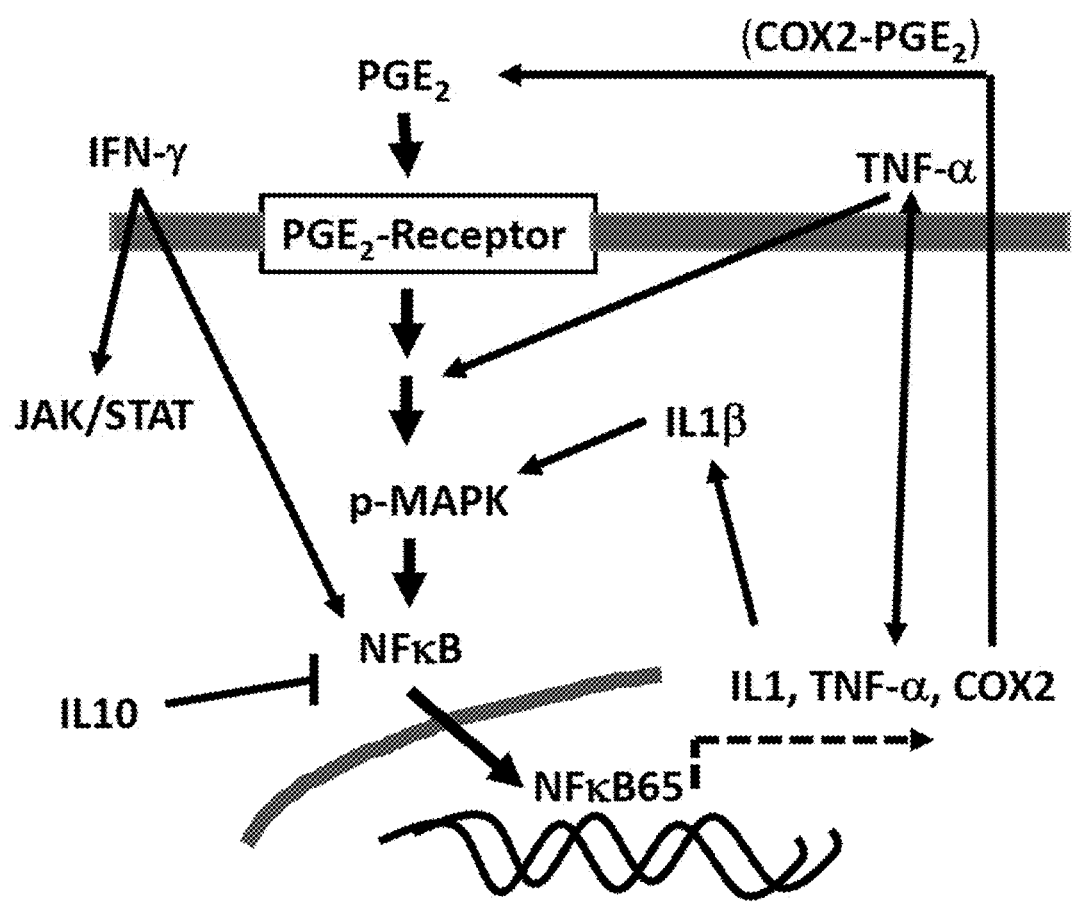
FIG. 15 is a schematic of factor-interplay in AD-associated neuro-inflammation.

We prioritized neuro-inflammation markers that are known to be upregulated (e.g., IFN-gamma, TNF-alpha, NFkappaB65, IL1-beta, IL6, COX-2) or downregulated (e.g., IL10) in the brains of human patients with AD. Overall, the neuro-inflammation markers are proposed to form feedback loops (FIG. 15). One messenger is Prostaglandin E$_2$ (PGE$_2$), which binds to the receptor and activates a cascade, leading to MAPK phosphorylation and activation of the NFkappaB 65kd subunit. The NFkappaB 65kd subunit translocates to the nucleus and activates downstream transcriptions of other inflammatory mediators, including IL1, TNF-alpha, and COX-2. COX-2, in turn, generates PGE$_2$. Inflammatory cytokine IL-1beta activates COX-2. TNF-alpha is also thought to activate p38MAPK Inflammatory cytokine Interferon-gamma (IFN-γ) leads to activations of JAK/STAT and NFkappaB.

Figure 4:
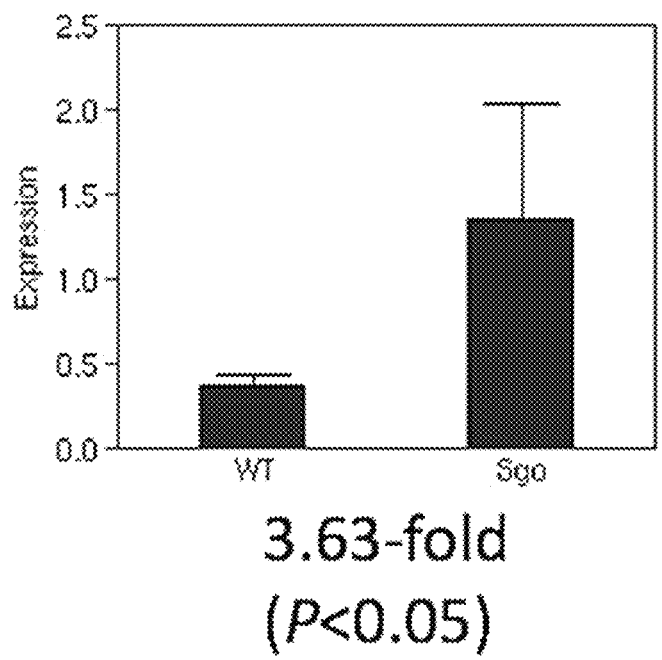
FIG. 4 is a graph showing that APBB1, a gene implicated in AD development, is over-expressed in whole blood RNA in 12-month-old Sgo1$^{-/+}$ mice (N=3) compared with wild-type mice (N=3), P<0.05. However, no significant AD pathology in the brain was observed at the time point (data not shown).

Expression of Amyloid-β Precursor Protein Binding Family B Member 1 (APBB1) in Middle-Aged Sgo1$^{-/+}$ Mice To identify biomarkers for CIN and cohesinopathy in whole blood RNA, we performed comparative whole blood RNAseq analysis on 12-month-old Sgo1$^{-/+}$ and wild-type mice. Among differentially expressed genes (P<0.05), Amyloid-β Precursor Protein Binding Family B Member 1 (APBB1) was notable, with a 3.63-fold increase compared with wild-type control (FIG. 4). APBB1 encodes a protein involved in DNA damage repair, interacts with APP, and is thought to promote AD. The pilot result at a younger age led us to suspect that the brains of Sgo1$^{-/+}$ mice would show signs of neurodegenerative disease similar to AD.

Sgo1$^{-/+}$ Brains Accumulated Amyloid-β by 24 Months of Age

Figure 1B:
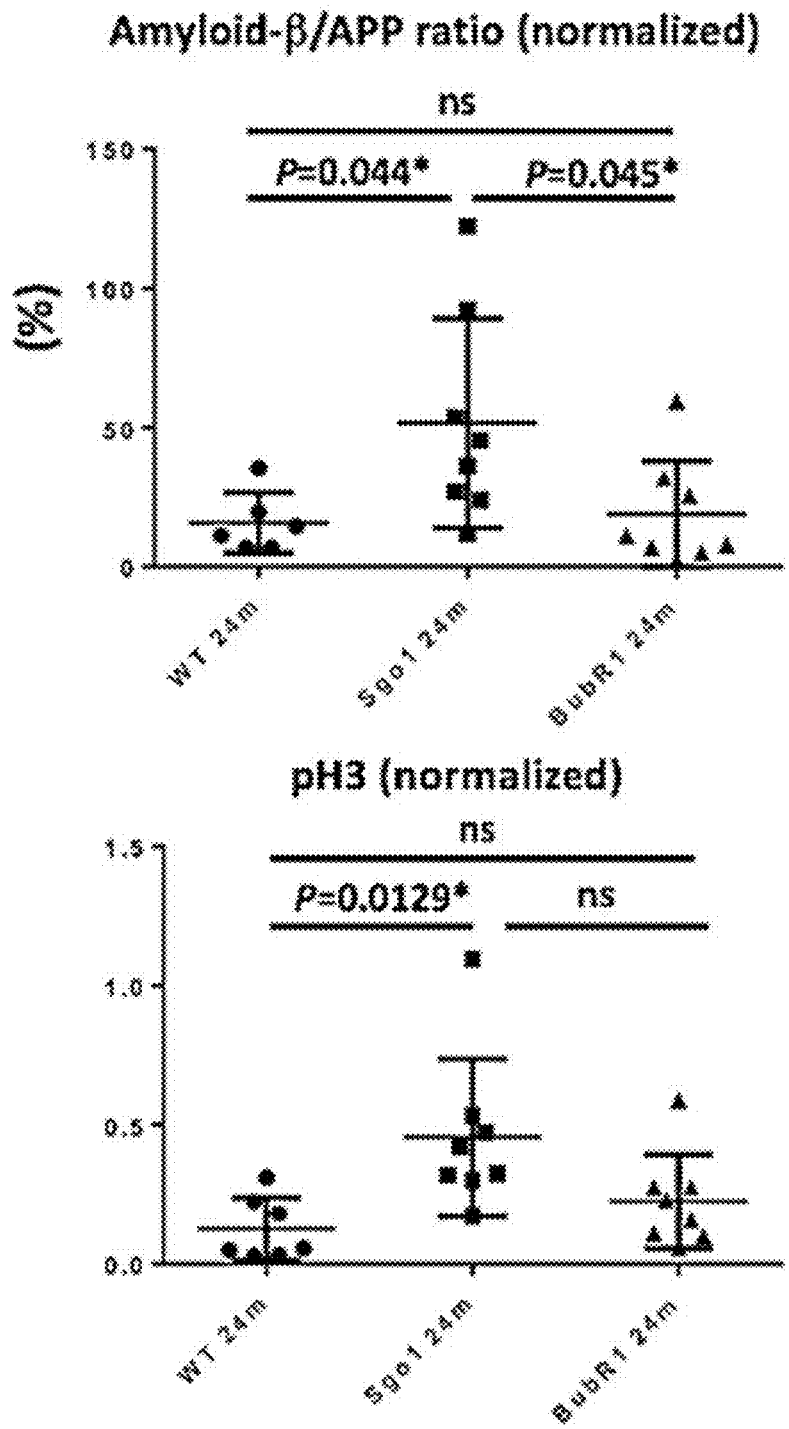
FIG. 1B shows amyloid-β/APP ratio and pH3 in the brains of FIG. 1A. Amyloid-β/APP ratio indicated significant accumulation of amyloid-β only in the $Sgo1^{-/+}$ brain. pH3 is most increased in $Sgo1^{-/+}$ mice, compared with WT and $BubR1^{-/+}$ mice.

An aging-and-carcinogenesis study cohort provided Sgo1$^{-/+}$ brains at older ages (24-25 months) corresponding to human old age over 65. We also collected brains from BubR1$^{-/+}$ haploinsufficient mice to determine whether they show brain aging and AD pathology, as the initial hypothesis focused on CIN and AD. Increased accumulations of amyloid-β (i.e., increase in amyloid-β/APP ratio) were observed in brain extracts from Sgo1$^{-/+}$ mice, but not from control littermate wild-type or BubR1$^{-/+}$ mice (FIGS. 1A, 1B). There was no significant difference in the total amount of phosphorylated Tau (FIG. 1A).

With the assumption that CIN would affect AD pathology, we were puzzled by the result that our haploinsufficient BubR1$^{-/+}$ model did not show more amyloid-β in the brain than did wild-type mice. A major difference between the Sgo1$^{-/+}$ cohesinopathy model and the BubR1$^{-/+}$ mitotic checkpoint defective model is the mitotic checkpoint function and existence (or absence) of prolonged mitosis. Sgo1$^{-/+}$ brains showed higher expression of mitotic marker phospho-HistoneH3 (p-H3), consistent with prolonged mitosis, while BubR1$^{-/+}$ brains did not (FIG. 1A-1B).

Mitotic Marker Phosphorylated Histone H3-Positive Cells are Enriched with Amyloid-β, p-Tau, and BACE (Beta-Secretase1)

Figure 2A:
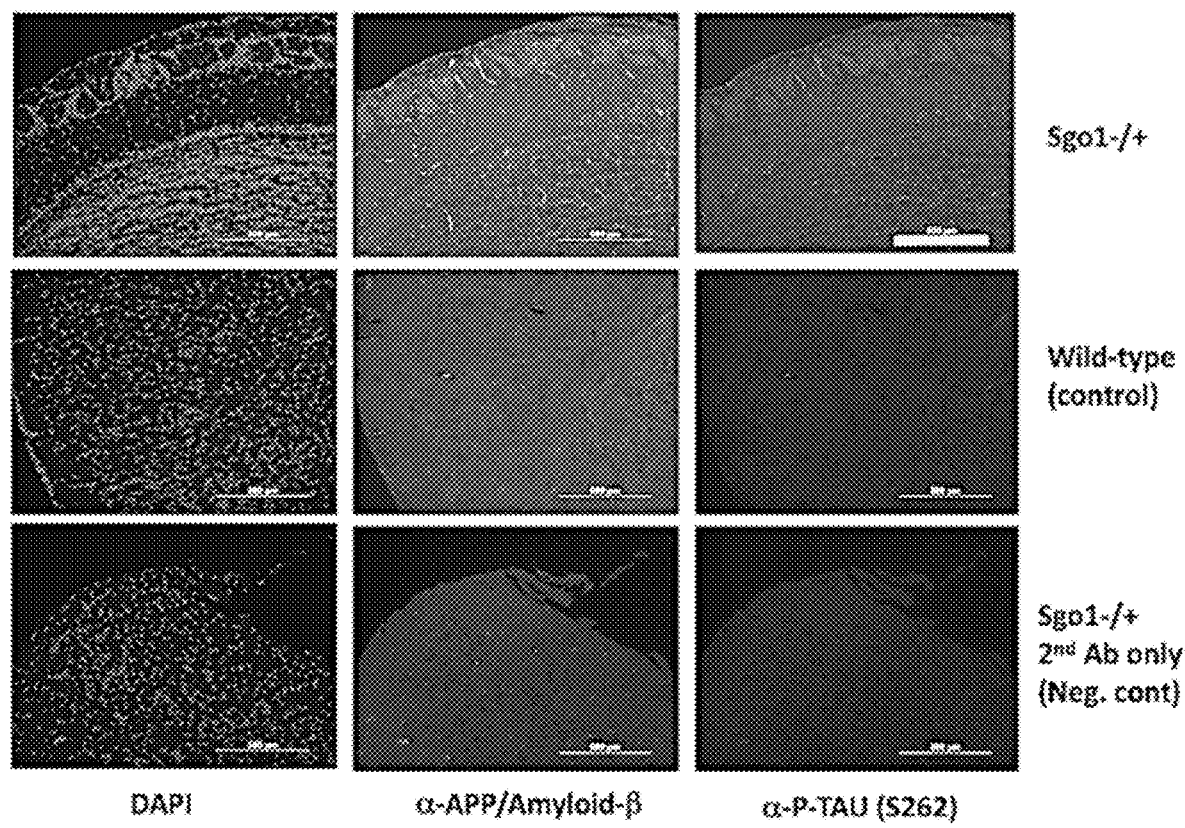
FIG. 2A shows micrographs of $Sgo1^{-/+}$ mouse brain tissue showing cells with APP/amyloid-β and phosphorylated Tau (Bar=500 μm).
Figure 2B:
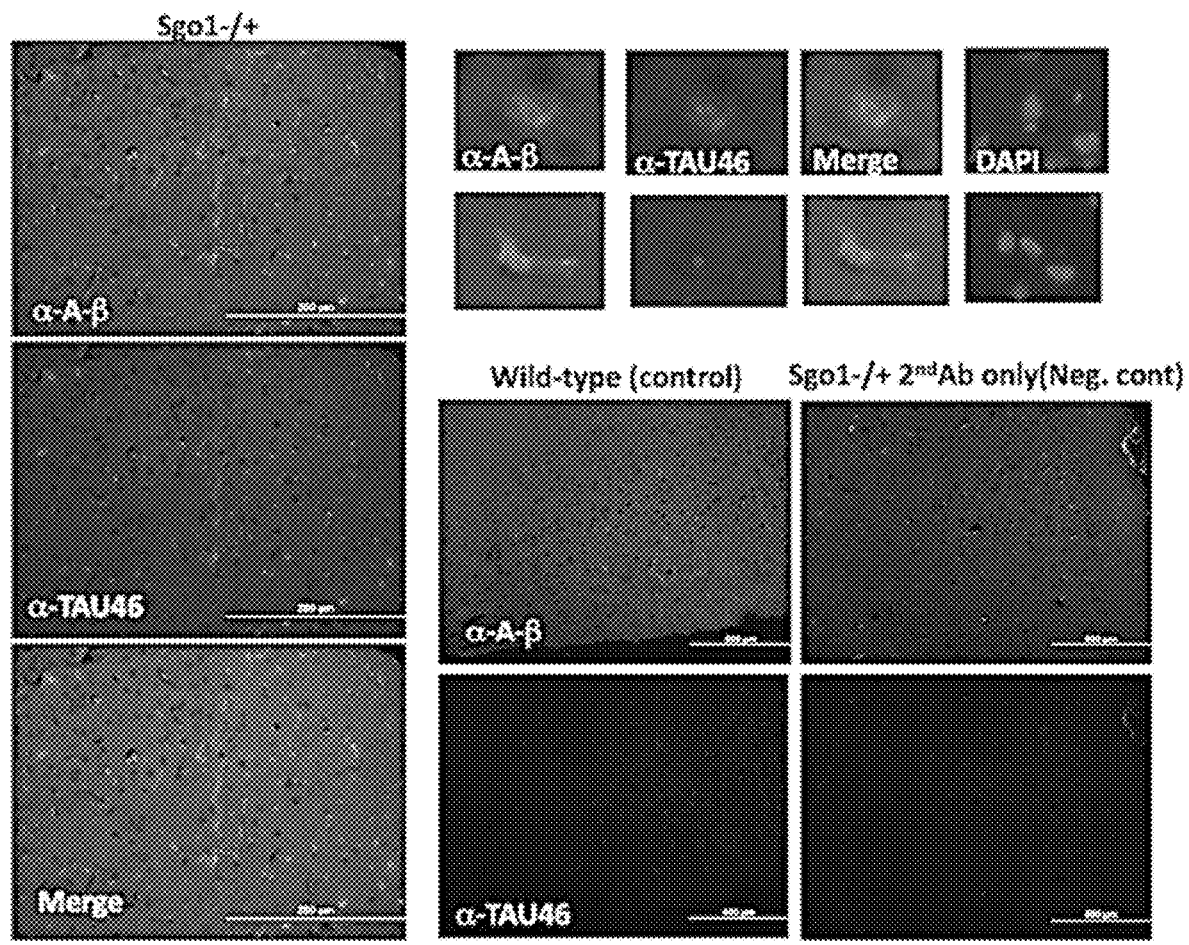
FIG. 2B shows micrographs of $Sgo1^{-/+}$ mouse brain tissue showing cells with amyloid-β and Tau. Although they generally co-localize and appear in vicinity, they do not always show exact co-localization (enlarged panels). Staining controls (wild type or $Sgo1^{-/+}$ without primary antibodies) provided much darker staining at the same image acquisition settings, except background signals from mouse IgG-expressing-infiltrating cells (Bar=500 μm).
Figure 2C:
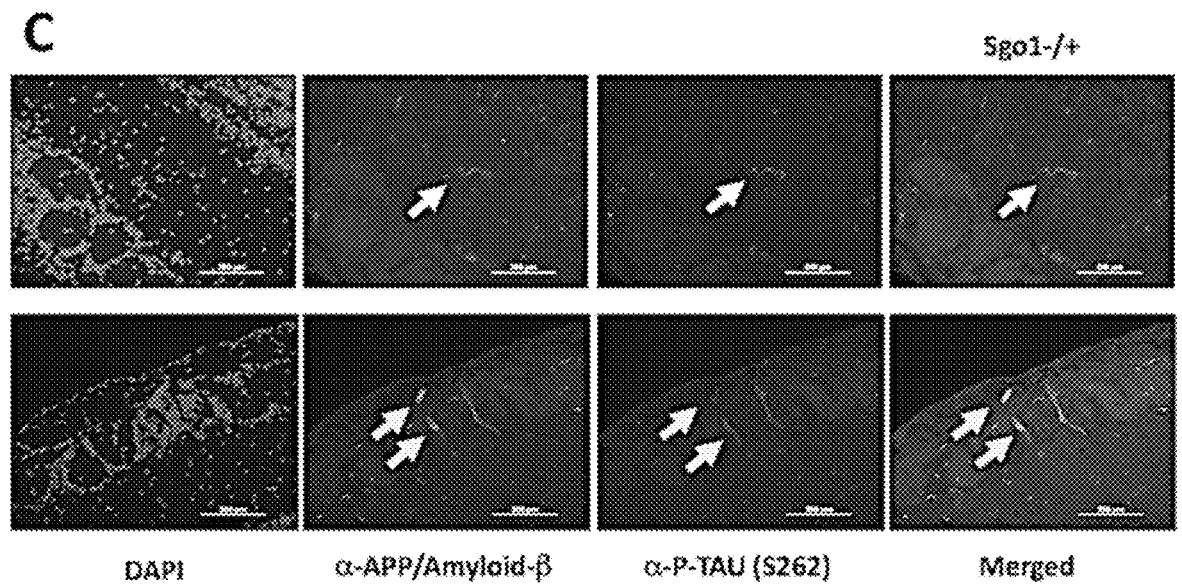
FIG. 2C shows micrographs of $Sgo1^{-/+}$ mouse brain tissue showing cells with APP/amyloid-β and phosphorylated Tau co-localized and appeared in extracellular matrix as a deposit (upper panel, white arrow) or in cells (lower panel, yellow arrows) (Bar=200 μm).
Figure 5:
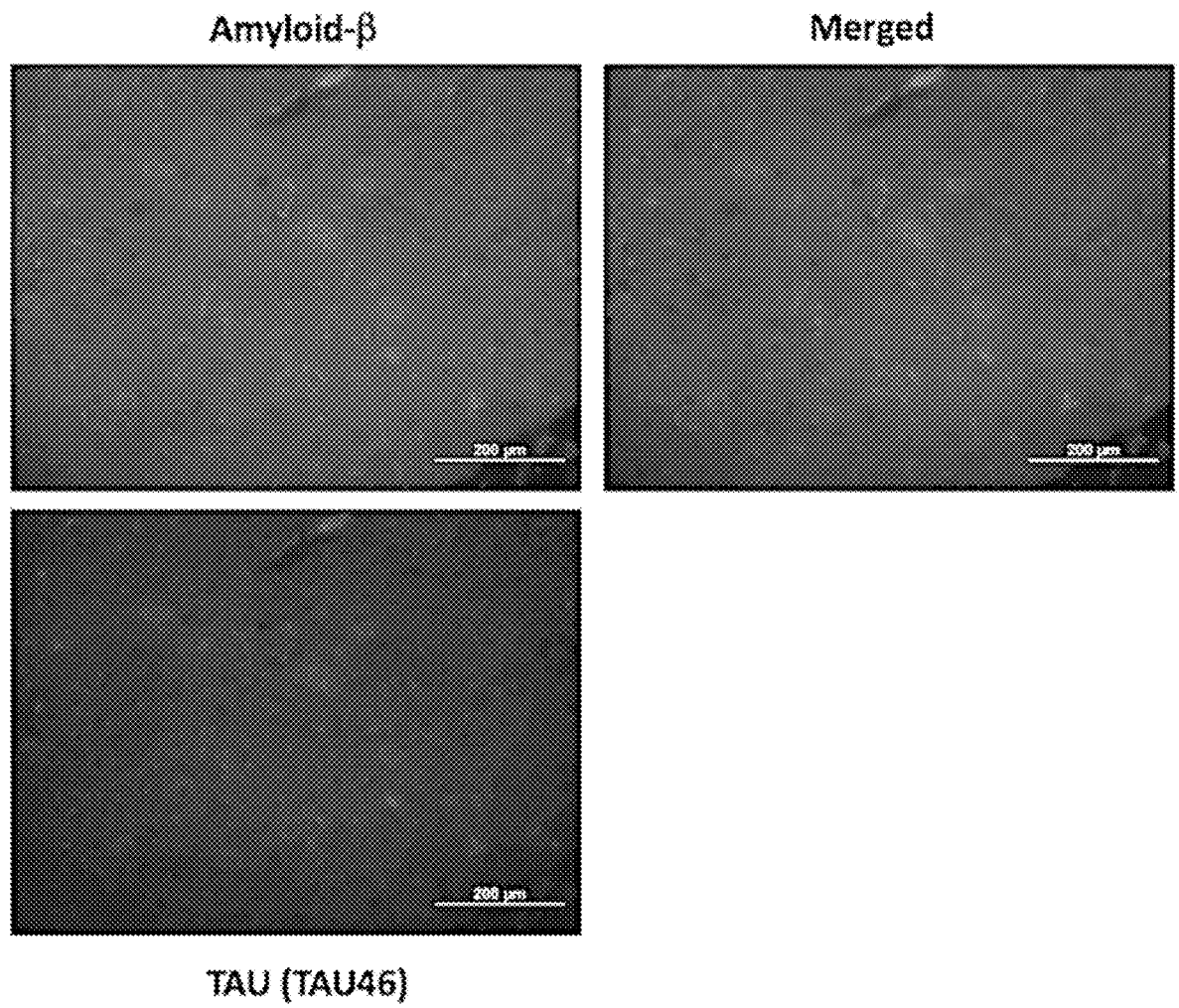
FIG. 5 shows mouse brain tissue micrographs of Amyloid-β and Tau co-localization in Sgo1$^{-/+}$ mice (confirmed with different antibody combinations). Presented at a higher magnification.
Figure 6:
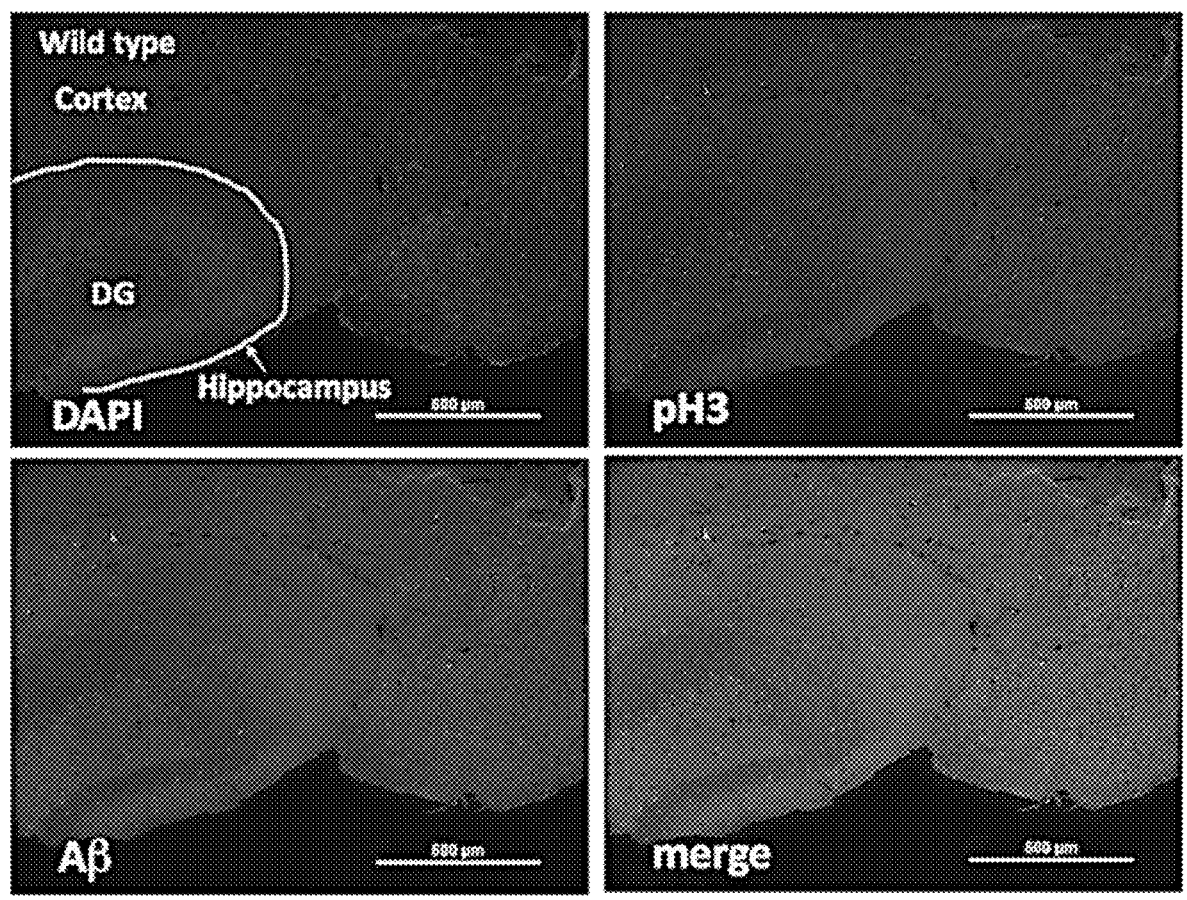
FIG. 6 shows mouse brain tissue micrographs of 24 month-old control wild type mice. p-H3 (mitotic) signals were observed exclusively in Dentate Gyms (DG) in the hippocampus, and hardly present in the cortex. Used as control for Sgo1$^{-/+}$ in FIG. 3A.

Immunofluorescence in Sgo1$^{-/+}$ mice indicated that APP/amyloid-β and Tau generally co-localized (FIG. 2A: phosphorylated Tau; FIG. 2B: Tau), and appeared in two forms: extracellular deposits and cytoplasmic staining enriched in living cells. In addition to amyloid-β deposits with p-Tau (FIG. 2C, upper panel), living cells co-expressing amyloid-β and p-Tau were observed (FIG. 2C, lower panel). These findings suggest that the source of amyloid-β/p-Tau deposits may be live cells accumulating both. FIG. 5 shows mouse brain tissue micrographs of Amyloid-β and Tau co-localization in Sgo1$^{-/+}$ mice (confirmed with different antibody combinations), presented at a magnification of 200 μm.

Figure 2D:
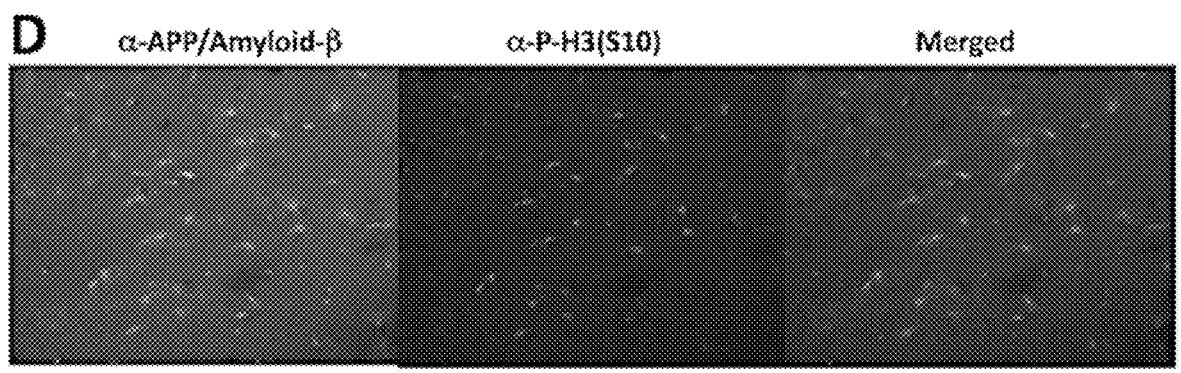
FIG. 2D shows micrographs of $Sgo1^{-/+}$ mouse brain tissue showing cells with APP/amyloid-β-positive cells or deposits are also positive for mitotic marker phosphorylated Histone H3 (Bar=200 μm).
Figure 2E:
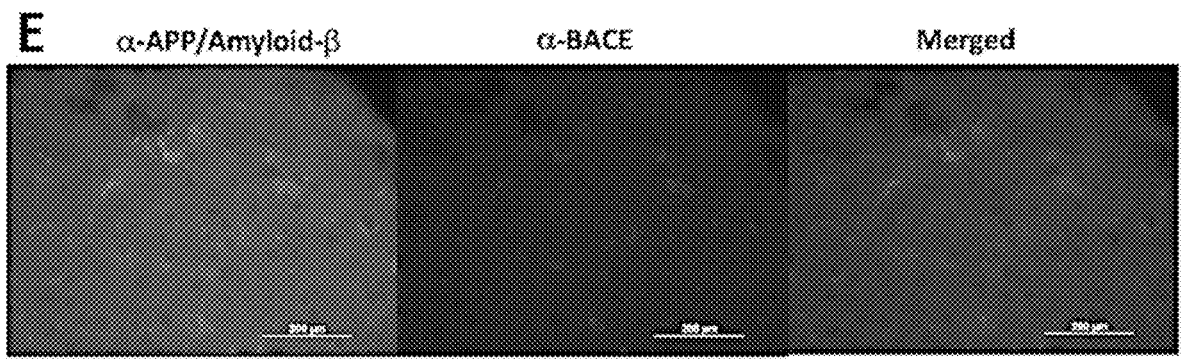
FIG. 2E shows micrographs of $Sgo1^{-/+}$ mouse brain tissue showing cells with APP/amyloid-β-positive cells or deposits are also positive for BACE (Bar=200 μm).

To explain the difference between Sgo1$^{-/+}$ and BubR1$^{-/+}$ models, we next hypothesized that prolonged mitotic arrest is the trigger for amyloid-β accumulation. The APP/amyloid-β-expressing cells were positive for mitotic marker p-H3 (FIG. 2D) and beta-secretase1 (BACE), an APP/amyloid-β conversion enzyme (FIG. 2E). The immunofluorescence results support the hypothesis that the source of accumulation of amyloid-β is p-H3-positive cells that also co-express BACE and p-Tau. Overall, the results suggested that amyloid-β and p-Tau originated from p-H3-positive (prolonged) mitotic cells.

Next we tested Congo red staining for amyloidosis, which did not provide clear staining in the Sgo1$^{-/+}$ (data not shown). Lack of Congo red staining suggested that degree of amyloid-β accumulation is not as high in this Sgo1$^{-/+}$ model as existing EOAD mouse models that typically express a few-to-several-fold amount of total Amyloids compared with controls and show Congo red staining. The result was in agreement with immunoblots in FIG. 1 indicating only mild increase in total Amyloids (Amyloid-β and APP combined) in Sgo1$^{-/+}$ compared with age-matched wild type and BubR1$^{-/+}$. The modest increase in total Amyloids suggest that the Sgo1$^{-/+}$ model may recapitulate relatively early phase of spontaneous LOAD development.

Expression of p-H3 in Brains of Sgo1$^{-/+}$ Mice

Figure 3A:
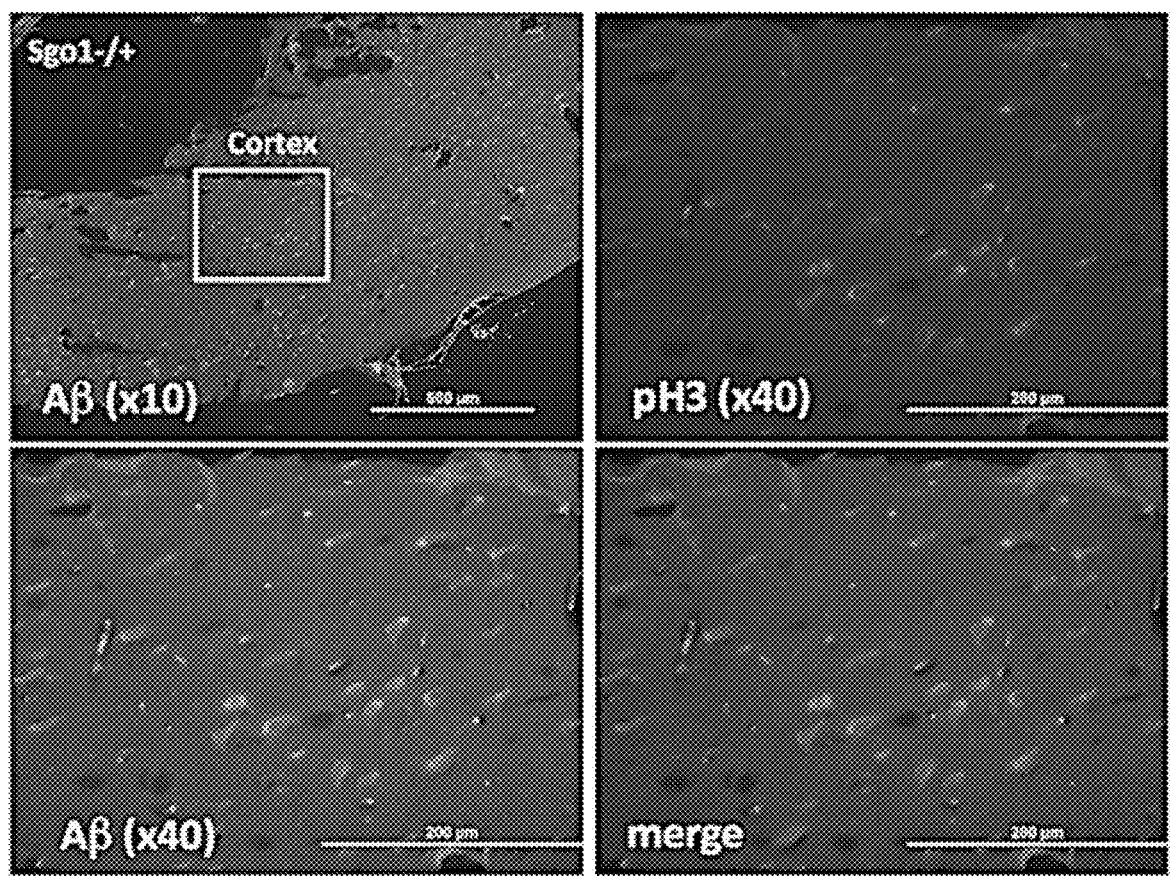
FIG. 3A shows micrographs of $Sgo1^{-/+}$ mouse brain tissue showing cells with accumulated amyloid-β-positive and p-H3-positive cells both in cortex and hippocampus, while in wild-type p-H3-positive cells exclusively located in hippocampus (FIG. 6). Amyloid-β-positive and p-H3-positive cells locate in the cortex of $Sgo1^{-/+}$. Cortex of $Sgo1^{-/+}$ were stained with amyloid-β, p-H3, and DAPI. Upper-left panel shows amyloid-β staining in a lower magnification (×10) (Bar=500 μm). The squared area is presented in a higher magnification (×40) in the other panels for Amyloid-β, p-H3, and merge (Bar=200 μm).
Figure 3B:
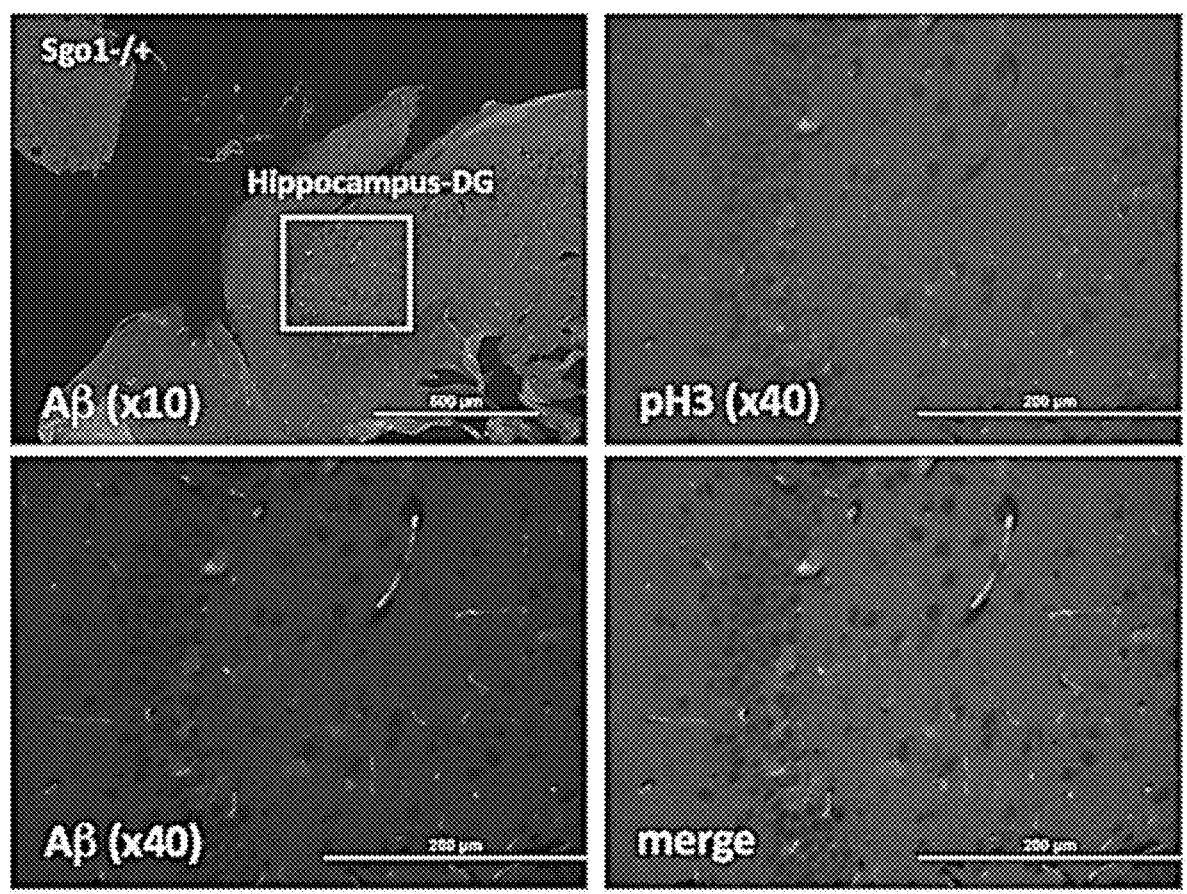
FIG. 3B shows micrographs of Sgo1$^{-/+}$ mouse brain tissue showing cells with accumulated amyloid-β-positive and p-H3-positive cells in the hippocampus.
Figure 3C:
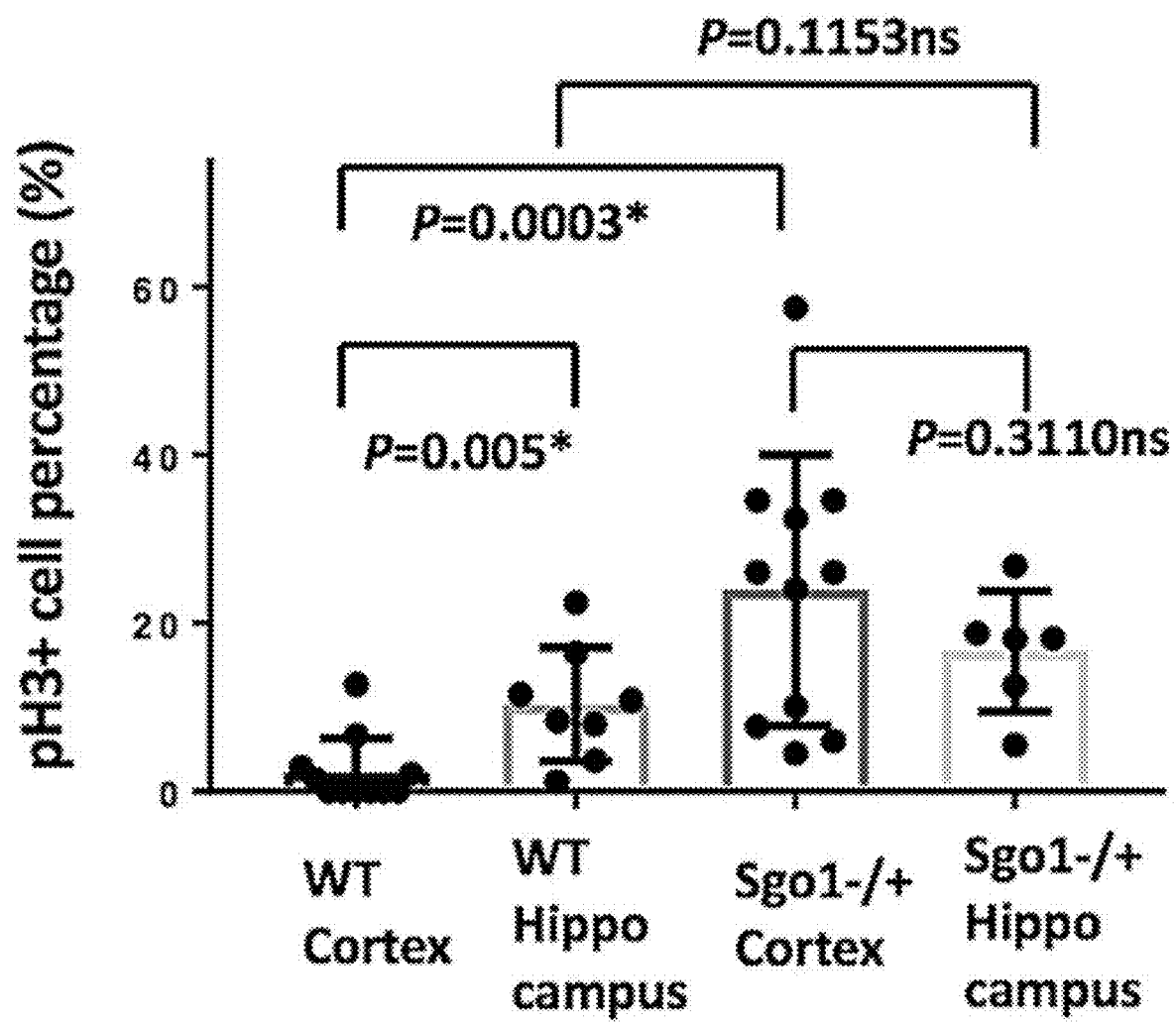
FIG. 3C is a graph showing quantification of p-H3-positive cells in the in cortex and hippocampus of both wild type and in Sgo1$^{-/+}$ mice. In wild-type brains (see FIG. 6), p-H3 signals located exclusively in hippocampus (P=0.005). In Sgo1$^{-/+}$ brains, high expression of p-H3 in the cortex was observed, hence p-H3 expression was not limited to hippocampus in Sgo1$^{-/+}$. Percentages of p-H3-positive cells in Sgo1$^{-/+}$ cortex were significantly higher compared with those in cortex of age-matched wild-type control (P=0.0003). Although p-H3 expression in hippocampus was modestly higher in Sgo1$^{-/+}$ compared with wild-type, the difference was not significant (P=0.1153). [Asterisk (*): P<0.05. ns (non-significant): P>0.05].

Dentate Gyms (DG) and subgranular zone in hippocampus are known to be sites for adult neurogenesis. Hippocampus is also known to be the site functionally affected by LOAD, leading to the primary LOAD symptom of memory defect. We tested whether amyloid-β-positive and p-H3-positive cells in Sgo1$^{-/+}$ localize in a particular area (e.g., hippocampus) in the brain. Amyloid-β-positive and-p-H3-positive cells in Sgo1$^{-/+}$ appeared both in the cortex and in the hippocampus (FIGS. 3A and 3B). The p-H3-positive cell percentages in Sgo1$^{-/+}$ were estimated as 23.96−/+15.32% in the cortex, and 16.64−/+6.48% in the hippocampus (FIG. 3C). In control wild-type (FIG. 6), amyloid-β-positive cells were hardly present, and p-H3-positive cells were localizing in the hippocampus (10.31−/+6.31%), but not in the cortex (2.33−/+3.82%) (FIG. 3C). The data demonstrate that amyloid-β-positive and p-H3-positive cells characteristically ($P<0.05$) appear in the cortex of Sgo1$^{-/+}$, although there is a modest (non-significant) increase of p-H3 in the hippocampus of Sgo1$^{-/+}$ compared with wild type as well.

Differential Gene Expression in Brains of Sgo1$^{-/+}$ Mice

To elucidate the molecular basis for the AD-associated brain pathology in Sgo1$^{-/+}$ mice, we used RNAseq to compare mRNA expression profiles in 24-month-old brains. With $P<0.05$ and 2-fold cut off, ten genes were identified. ARC, PMCH, Gm20388, and AA465934 were over-expressed, while Shisa8, Ebf3, DAO, S1c6a5, PPP1r17, and PCP2 were under-expressed (see FIG. 4 and Table 1 in provisional application 62/680,114). Among the ten genes, seven had known connections to AD and/or neuronal function.

Over-Expressed Genes in Sgo1$^{-/+}$ Mice

Activity Regulated Cytoskeleton Associated Protein (ARC), which had a 2.97-fold increase, is proposed to participate in AD pathogenesis, because ARC is required for activity-dependent generation of amyloid-β and genetic deletion of ARC (−/−) reduces amyloid-β load in a transgenic mouse model of AD (APP$_{SWE}$;PS1ΔE9). ARC upregulation was observed in human AD brain and may directly promote amyloid-β generation, explaining the pathology in Sgo1$^{-/+}$ mice, at least in part. The pro-melanin concentrating hormone (PMCH), which had a 29.44-fold increase, is processed proteolytically to generate multiple neuropeptides, and may regulate energy homeostasis and behaviors such as hunger, reproductive function, and sleep. The functions of Gm20388, which had a 3.55-fold increase, and AA465934, which had a 4.83-fold increase, remain unclear. The Gm20388 product carries partial homology to Low Density Lipoprotein Receptor Class A domain (LDLa) and may be involved in cholesterol metabolism, an AD-associated pathway.

Under-Expressed Genes in Sgo1$^{-/+}$ Mice

Shisa Family Member 8 (Shisa8), which had a 4.15-fold decrease, is a Shisa-family transmembrane protein, which may be involved in Wnt/FGF signaling or neurotransmitter regulation. Early B-cell factor 3 (Ebf3), which had a 11.63-fold decrease, encodes a transcription factor and may be associated with LOAD ($p=0.03$). Mutations in Ebf3 disturb transcriptional profiles and cause intellectual disability, ataxia, and facial dysmorphism in humans. D-Amino Acid Oxidase (DAO), which had a 44.79-fold decrease, removes the D-amino acids that accumulate during aging. DAO degrades D-serine, a co-agonist of the NMDA receptor, and is associated with schizophrenia. A DAO inhibitor Sodium benzoate improved cognitive and overall functions in early-phase AD patients. Reduced DAO expression may play a compensating role against the AD-like pathology in Sgo1$^{-/+}$ model mice. Solute Carrier Family 6 Member 5 (S1c6a5), which had a 145.07-fold decrease, is a sodium- and chloride-dependent glycine neurotransmitter transporter. S1c6a5 physically interacts with Syntaxin1A, which binds to Presenilin1, mutations in which are linked to familial AD. S1c6a5 is also a component of the NRF2 pathway involved in oxidative stress response. Mutations in S1c6a5 cause hyperekplexia, a neurological disorder with pronounced startle responses and neonatal apnea. Protein Phosphatase 1 regulatory subunit 17 (PPP1r17)/G-substrate, which had a 13.11-fold decrease, is a protein phosphatase inhibitor primarily expressed in Purkinje cells. PPP1r17 is reportedly involved in hypercholesterolemia, long-term depression, and attenuation in the long-term adaptation of optokinetic eye movement response. Protein phosphatase 1 can dephosphorylate p-Tau. Under-expression of PPP1r17 may play a compensatory role against AD-like pathology via dephosphorylating p-Tau. PCP2 (Purkinje Cell Protein 2) which had a 24.01-fold decrease, may function as a modulator for G protein signaling. However, PCP2$^{-/-}$ knockout mice showed no phenotype, making elucidation of the function difficult.

Without wishing to be bound by theory, the results provided herein suggest that accumulated Amyloid-β originated from p-H3-positive prolonged mitotic cells, which later die and leave extracellular deposits including Amyloid-β and p-Tau that may become seeds for "plaques and tangles". Cells with accumulated Amyloid-β were specifically observed in Sgo1$^{-/+}$+ model mice with intact spindle checkpoint, and not in mitotic checkpoint-defective BubR1$^{-+}$ model mice. There is supporting evidence suggesting that mitotic cells are involved in Amyloid-β accumulation in human LOAD: (a) Human neurofibrillary tangles co-localized with MPM2 antigens, another mitotic marker, (b) Abnormal Tau phosphorylation of the Alzheimer-type also occurred during mitosis in human neuroblastoma SY5Y cells overexpressing Tau, (c) APP$^{Thr668}$ phosphorylation in mitosis correlated with increased processing of APP to generate Aβ and the C-terminal fragment of APP, (d) Although p-H3 localization is usually limited in chromatin in many other organs, human AD brain showed a cytoplasmic, diffused pattern of p-H3, which was recapitulated in the Sgo1$^{-/+}$ mouse brain (FIGS. 2D, 3A and 3B). These reports strongly suggest that human LOAD development can be aided by prolonged mitosis, which the Sgo1$^{-/+}$ model recapitulates. Indeed, in human LOAD models incorporating the critical role of mitotic cells have been proposed, such as a "simple linear model" that states that human AD pathology develops from mitotic cycle-reentering neurons that later die, and the "two-hit model" of human LOAD that purports that LOAD development occurs with (i) oxidative stress and (ii) mitotic re-entry. Although the direct trigger for mitotic cycle reentry in Sgo1$^{-/+}$ model mice remains unclear, studies on roles of cell cycle regulators, such as Cdk5, and on effects of genes identified through RNAseq in this study on the cell cycle, are warranted.

The Sgo1$^{-/+}$ haploinsufficient mouse is a model that displays two direct effects of a reduction in Sgo1, both of which lead to prolonged mitosis via the spindle checkpoint: (1) cohesinopathy in mitotic chromosome, and (2) defects in centrosome integrity. Cohesinopathy in humans leads to diseases with cancer-proneness, developmental malformation, and/or intellectual disability and behavioral issues, such as Cornelia de Lange syndrome or mutations in STAG1 or STAG2. The symptoms suggest that maintenance of chromosome cohesion may play a role more critical than previously anticipated in brain functions.

Experimental Series II

Materials and Methods

Samples

Twenty-four-month-old animals and brain tissue samples were obtained as described above. Twelve-month-old animals and brain tissue samples were obtained from a previous study described in Yamada et al., (Yamada H Y, Zhang Y, Reddy A, Mohammed A, Lightfoot S, Dai W, et al., 2015. Tumor-promoting/progressing role of additional chromosome instability in hepatic carcinogenesis in Sgo1 (Shugoshin 1) haploinsufficient mice. Carcinogenesis. 2015; 36(4): 429-40.). Fifteen- and eighteen-old Sgo1$^{-/+}$ brain tissue samples were obtained in this study (N=4 each). Samples used for immunohistochemistry or immunofluorescence were preserved in 10% buffered formalin, then were embedded in paraffin and processed onto slides in the CCPDD histopathology core. Samples used for select pathway protein panel analyses were flash-frozen in liquid nitrogen, and stored at −80° C.

Immunoblots, Immunohistochemistry and Immunofluorescence

For Immunoblots and immunofluorescence, procedures described as above were followed. For immunoblot control, rat/mouse amyloid-beta1-42 synthetic peptide (Abcam, Cambridge, MA, USA. ab120959) was used. Since formalin-fixed aged brain samples tend to generate high autofluorescence, sodium borohydride and CuSO$_4$ treatments were included as our standard procedures for immunofluorescence. For immunohistochemistry, we used SuperPicture 3$^{rd}$ gen IHC kit (ThermoFischer Scientific, Waltham, MA, USA) following manufacture's protocol. We used the following primary antibodies; amyloid-beta (referred as B-4; Santa Cruz Biotechnology, Dallas, TX, USA. Cat. number sc-28365), amyloid-beta (referred as NAB228; Cell Signaling Technology, Danvers, MA, USA. #2450), amyloid-beta (referred as D54D2; Cell Signaling Technology, #8243), p21$^{WAF1/CIP1}$ (Santa Cruz, sc-817), IFN-gamma (Bioss antibodies, Woburn, MA bs-0480R), TNF-alpha (Bioss, bs-2081R), NFkappaB 65kd (Santa Cruz, sc-372), IL1-beta (Bioss, bs-6319R), IL10 (Bioss, bs-0698R), phosphor-p38MAPK [T180+Y182] (Bioss, bs-2210R), Actin (Santa Cruz, sc-1616), COX-2 (Santa Cruz, sc-7951), IL-6 (Bioss, bs-0379R), and p-TAU(S262) (EnoGene, New York, NY, USA. E011111).

Pathway Protein Panel Analysis

Frozen mouse brains (mouse cerebrum including cortex and hippocampus, and excluding olfactory bulb, cerebellum, medulla) were extracted in RIPA buffer with 250 mM NaCl, with added protease inhibitor cocktail (Sigma-Aldrich, St. Louis, MO, USA) and proteasome inhibitor MG132 10 μM (Sigma-Aldrich). Extracts were cleared with 5000 rpm for 5 minutes, and protein concentrations of the supernatants were estimated with a Nanodrop spectrophotometer (Thermo Fischer Scientific, Waltham, MA, USA). The supernatants were submitted to the Multiplexing Protein Quantification Core facility at the Oklahoma Medical Research Foundation (Oklahoma City, OK, USA) for protein panel analyses with quantitative mass spectrometry (TSQ Quantiva triple quadrupole mass spectrometry system).

Quantitative Mass Spectrometry

The samples were mixed with 100 μL 1% SDS, 20 μL of our Bovine Serum Albumin (BSA) internal standard, mixed, and heated for 15 min. The proteins precipitated with 1 mL acetone. The dried protein pellet was reconstituted in 60 μL Laemmli sample buffer and 20 μL (20 μg) used to run a short (1.5 cm) SDS-PAGE gel. The gels were fixed and stained. Each sample was cut from the gel as the entire lane and divided into smaller pieces. The gel pieces were washed to remove the Coomassie blue then reduced, alkylated, and digested overnight with trypsin. The mixture of peptides was extracted from the gel, evaporated to dryness in a SpeedVac and reconstituted in 200 μL 1% acetic acid for analysis. The analyses were carried out on a TSQ Quantiva triple quadrupole mass spectrometry system. The HPLC was an Ultimate 3000 nanoflow system with a 10 cm×75 μm i.d. C18 reversed phase capillary column. 5 μL aliquots were injected and the peptide eluted with a 60 min gradient of acetonitrile in 0.1% formic acid. The mass spectrometer was operated in the selected reaction monitoring mode. For each protein, the method was developed to measure 2 ideal peptides. Assay for multiple proteins were bundled together in larger panels. Data were analyzed using the program Skyline to determine the integrated peak area of the appropriate chromatographic peaks. The response for each protein was calculated as the geometric mean of the peptide areas. These values were normalized to the response for the BSA standard and to the total ion current. The samples were also analyzed on our Thermo QEx system in the LC-full scan MS mode. The total ion current in those analyses is an indication of the amount of material present in the sample and may be useful for normalization. For final analysis, we used total ion current for normalization, as we found some variations among BSA signals. Additional 'universal detection' runs, high resolution accurate mass (HRAM) were also done using our orbitrap system (ThermoScientific QEx plus), as an addition type of data that can be re-interrogated as needed.

Overall, as above, four groups ("12-month-old wild-type", "12-month-old Sgo1$^{-/+}$", "24-month-old wild-type", and "24-month-old Sgo1$^{-/+}$"; N=5 each) with a total of 20 samples were simultaneously processed for quantification. The amounts of proteins (i.e., representative peptides) in the panels were quantified. Total ion current was used for normalization. An antioxidant protein panel (49 proteins), a mitochondria and energy metabolism panel (47 proteins), and a beta-oxidation and peroxisome panel (37 proteins) were analyzed. Subtracting overlapping proteins in the panels, a total of 130 proteins were analyzed.

Cohorts Comparison

To identify differences among the four groups, normalized peptide reads were analyzed with a series of group-to-group comparisons; (i) "12-month-old wild-type" vs. "12-month-old Sgo1$^{-/+}$", (ii) "24-month-old wild-type" vs. "24-month-old Sgo1$^{-/+}$", (iii) "12-month-old wild-type" vs. "24-month-old wild-type", and (iv) "12-month-old Sgo1$^{-/+}$" vs. "24-month-old Sgo1$^{-/+}$", with GraphPad Prism 7 software (ver7.03) (San Diego, CA, USA). Unpaired t-test results with N=5, P<0.05, calculated by the software, were considered significant. Simultaneous multiple comparisons (e.g., two-way ANOVA) were not employed, as appropriate correction method factoring both age-associated effects and strain-associated effects has not been determined.

Results

Figure 7:
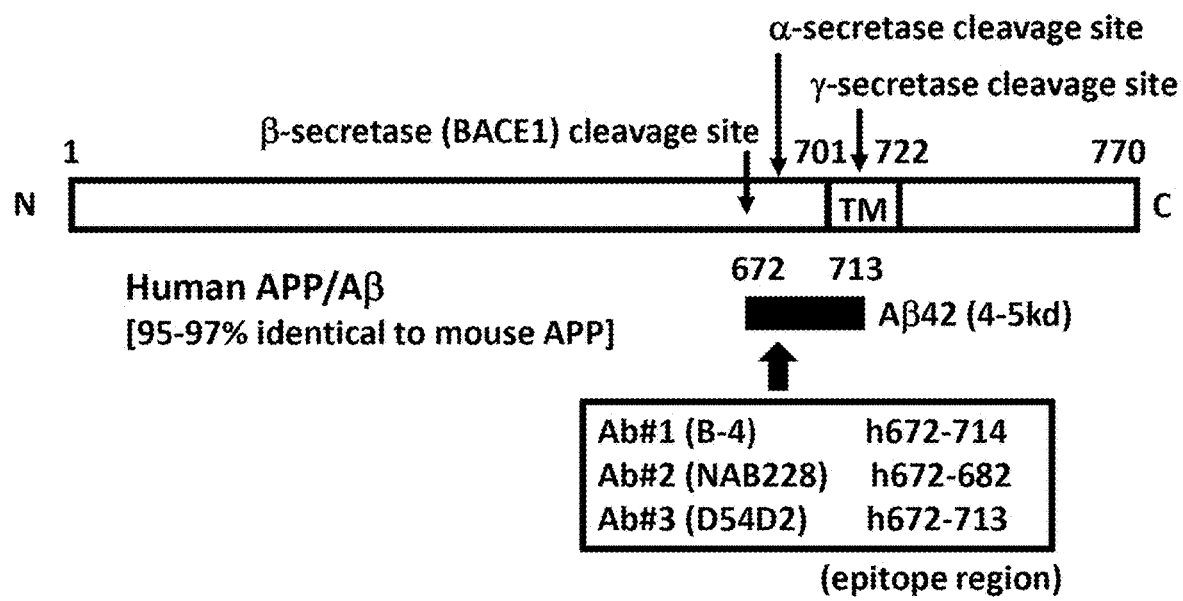
FIG. 7 shows a schematic of human/mouse APP structure. Anti-Amyloid-β antibodies (B-4, NAB228, D54D2) were generated against various portions of human amyloid-β, which is 97% identical to mouse amyloid-β.
Figure 8:
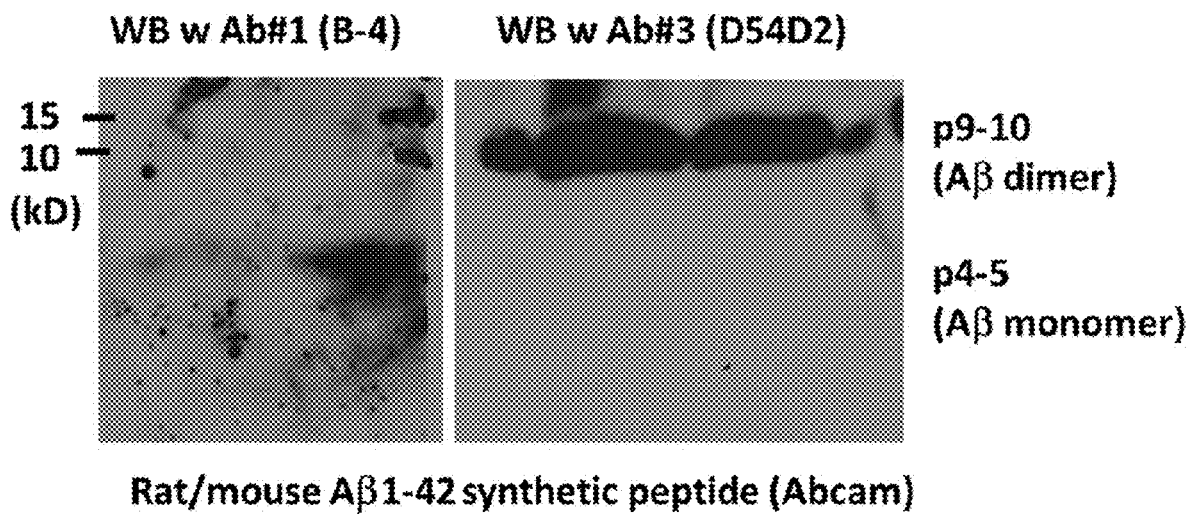
FIG. 8 shows gels demonstrating that synthetic rat/mouse amyloid-β$^{1-42}$ peptide was recognized by anti-Amyloid-β antibodies. Amyloid-β can form SDS-resistant oligomers that may expose epitope regions differently. B-4 antibody preferentially recognized monomer (p4-5), while D54D2 recognized dimer (p9-10).
Figure 9:
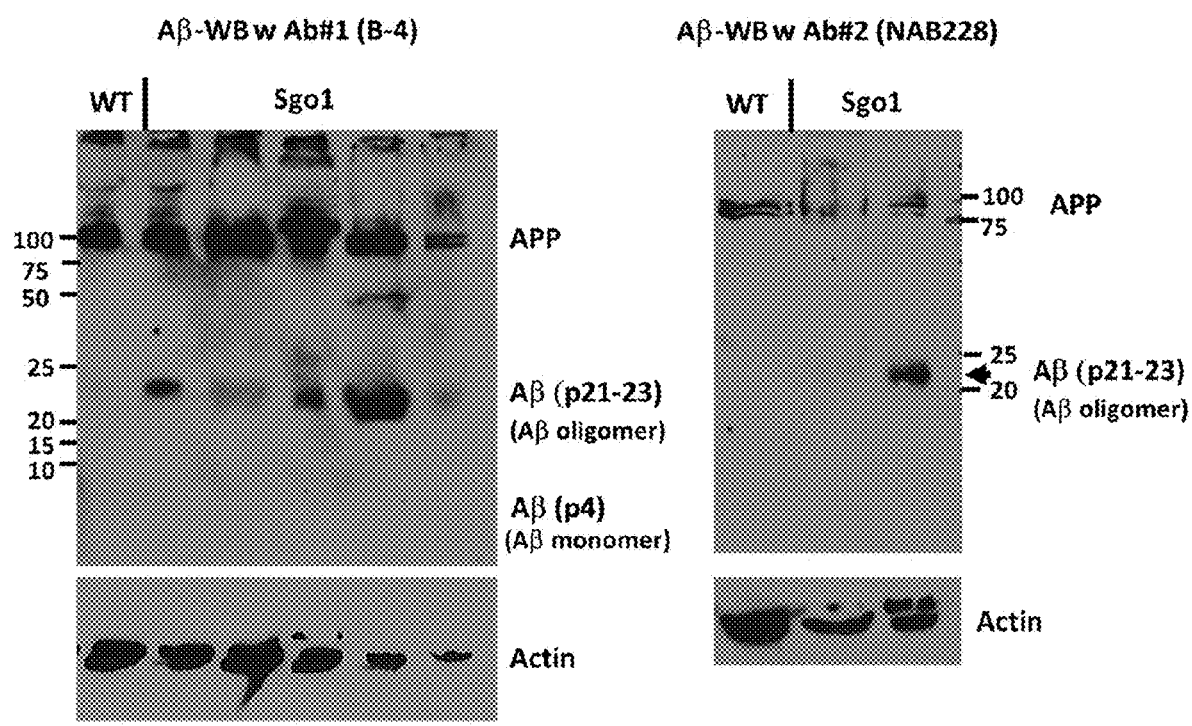
FIG. 9 shows gels that demonstrate 24-month-old Sgo1$^{-/+}$ brain extracts contained amyloid-β p21-23. Both anti-amyloid-β antibodies, B-4 (left panel) and NAB228 (right panel), detected APP and amyloid-β p21-23 in immunoblots. Age-matched wild type detected only APP.
Figure 10:
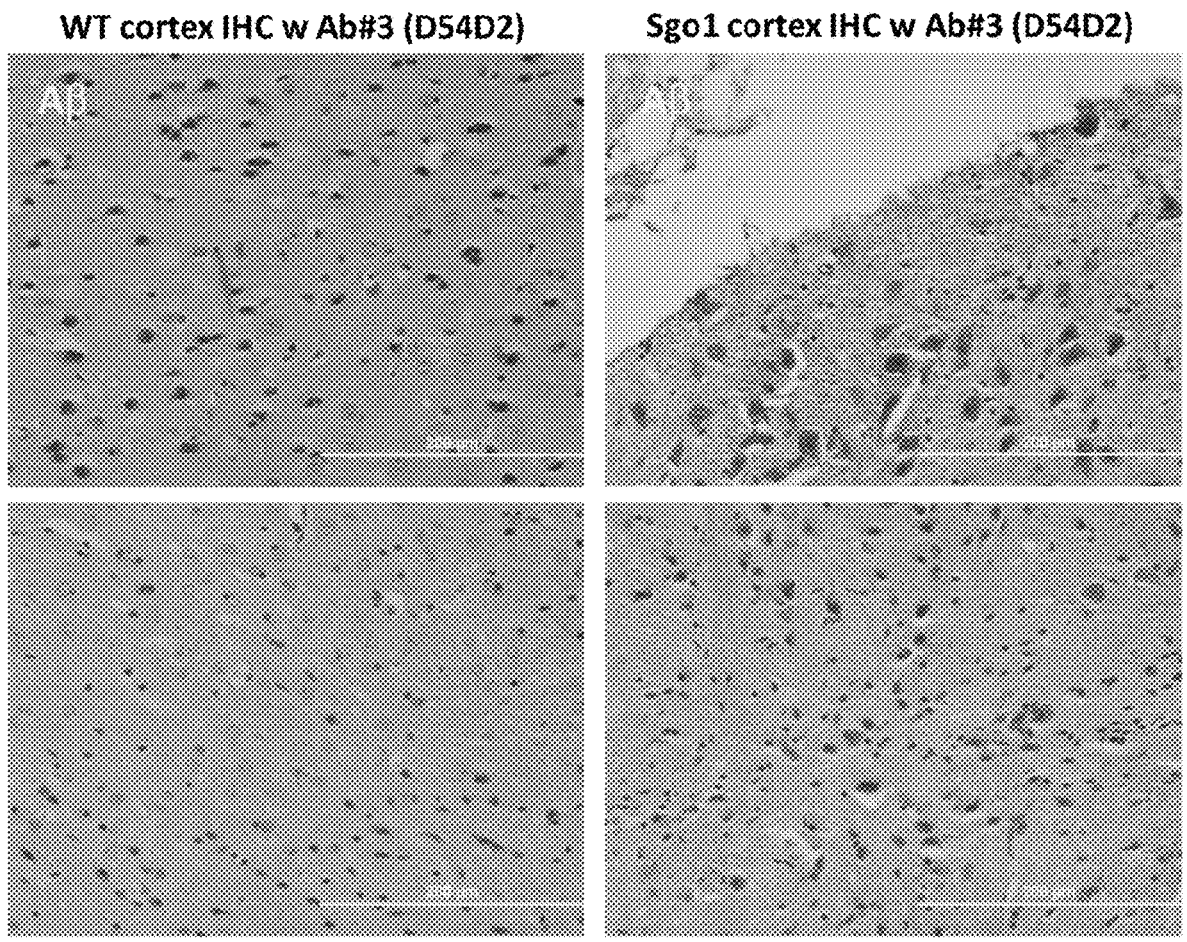
FIG. 10 shows micrographs of twenty-four month-old Sgo1$^{-/+}$ brain showing amyloid-β accumulation in IHC. Control age-matched wild type did not show IHC positive staining.
Figure 11:
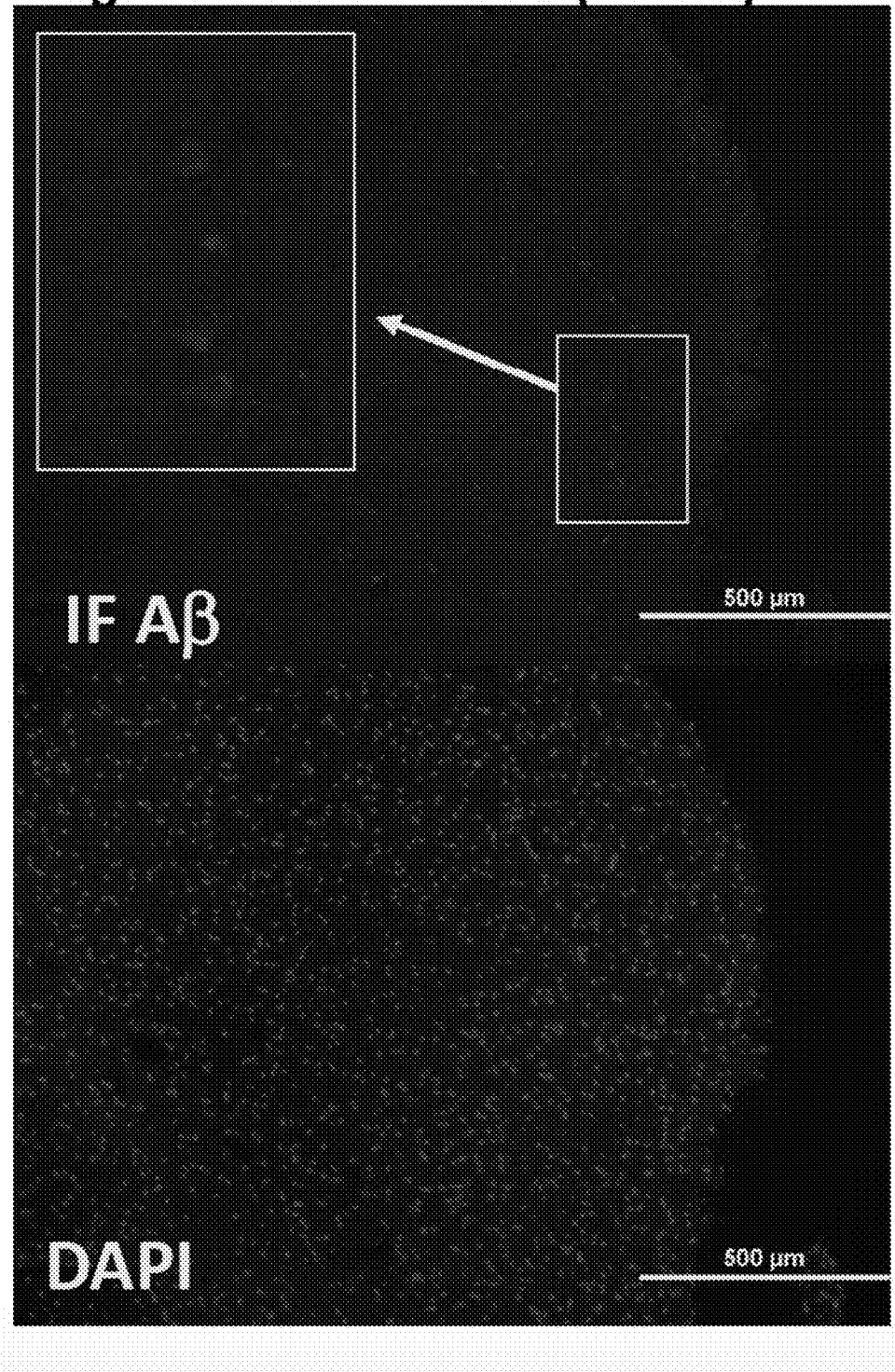
FIG. 11 is a micrograph of a twenty-four month-old Sgo1$^{-/+}$ brain showing amyloid-β accumulation in IF. IF showed positive signals in Sgo1$^{-/+}$ brain, consistent with IHC results. Control wild type did not show clear signals with equalized image acquisition settings (not shown).

Mouse APP is 97% identical to human APP. To verify amyloid-beta accumulation in mice, we used three commercial antibodies for human amyloid-beta (B-4, NAB228, and D54D2), with synthetic rat/mouse amyloid-beta peptide as control (FIG. 7). This series of experiments verified that these antibodies against human amyloid-beta recognize mouse amyloid-beta. In immunoblots, amyloid-beta can form SDS-resistant oligomers and can appear in monomer (p4-5), dimer (p9-10) and higher molecular weight oligomer. B-4 antibody preferentially recognized p4-5 monomer form of mouse synthetic amyloid-beta, while D54D2 recognized p9-10 dimer form (FIG. 8). In addition to oligomerization, in vivo, APP can be cleaved by a variety of proteases (e.g., $\alpha$-, $\beta$-, $\delta$-, $\eta$-secretases, Neprilysin/CD10), which can lead to generations of protein fragments of different sizes. We tested 24 month-old $Sgo1^{-/+}$ brain extracts with the antibodies. Control age-matched wild type showed only full-length APP (p87) and no shorter form, while $Sgo1^{-/+}$ brain showed p21-23 in addition to APP. Both B-4 and NAB228 antibodies indicated the same sized band of p21-23, which we interpret as an oligomer form of mouse amyloid-beta (FIG. 9). We also tested localization of the mouse amyloid-beta with immunohistochemistry (IHC) (FIG. 10) and immunofluorescence (IF) (FIG. 11). As in immunoblots, wild type control did not show IHC-positive signals, while $Sgo1^{-/+}$ brains showed IHC positive signals in cell bodies (FIG. 10). Results of IF with equalized acquisition settings were consistent with IHC; no signal detected in wild type, while IF-positive cells were observed in $Sgo1^{-/+}$ brains (FIG. 11). Thus, the results indicate that IHC/IF procedure-resistant form of mouse amyloid-beta accumulates in aged $Sgo1^{-/+}$ mouse brains.

Figure 12:
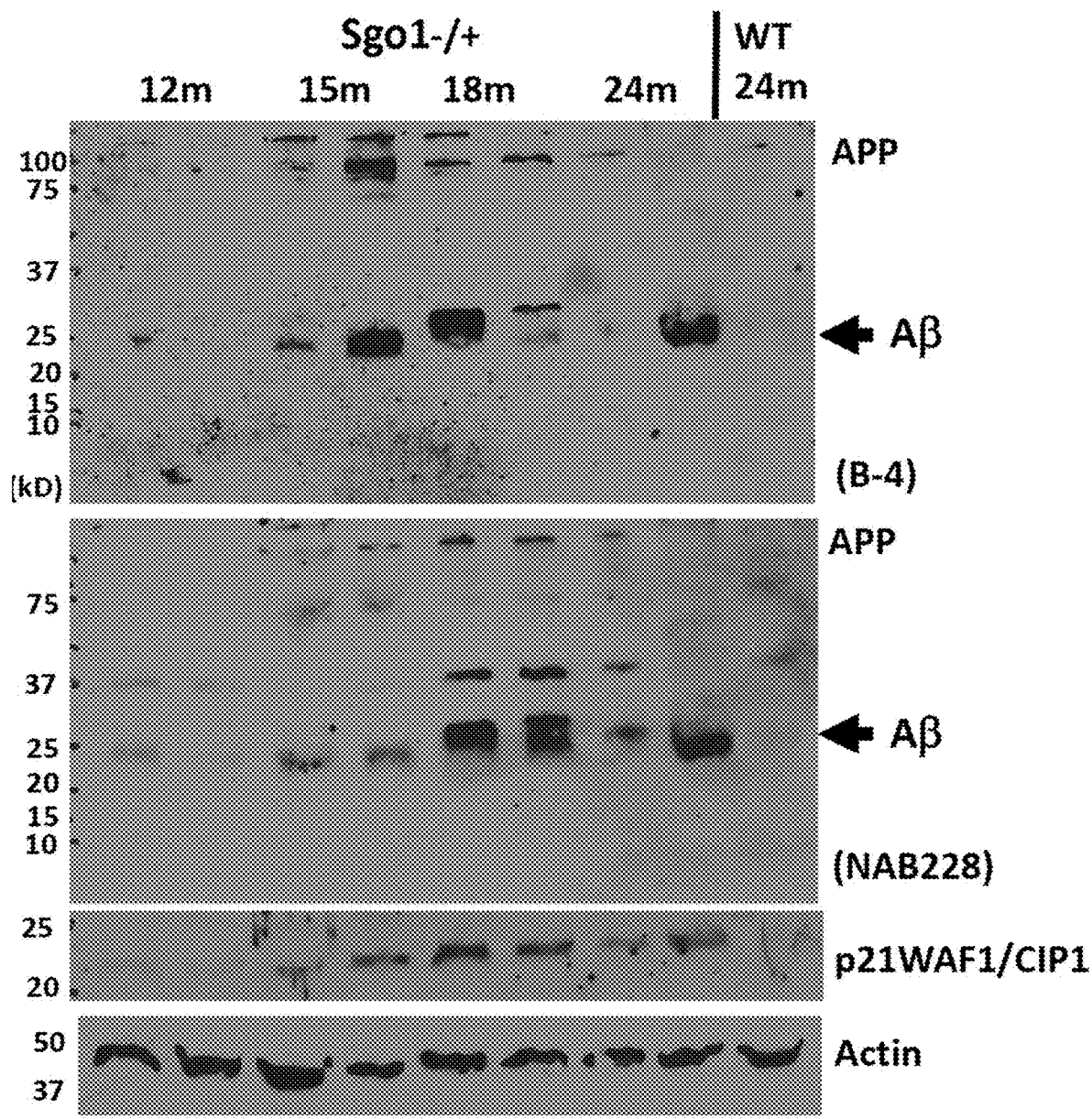
FIG. 12 show gels demonstrating that cerebral amyloid-β accumulated by 18 months of age in Sgo1$^{-/+}$ mice. Extracts were prepared from brains from Sgo1$^{-/+}$ mice of 12, 15, 18, and 24 months of age, and probed for amyloid-β (with B-4, top panel), amyloid-beta (with NAB228, middle panel), aging marker p21$^{WAF1/CIP1}$, and actin (loading control).
Figure 13:
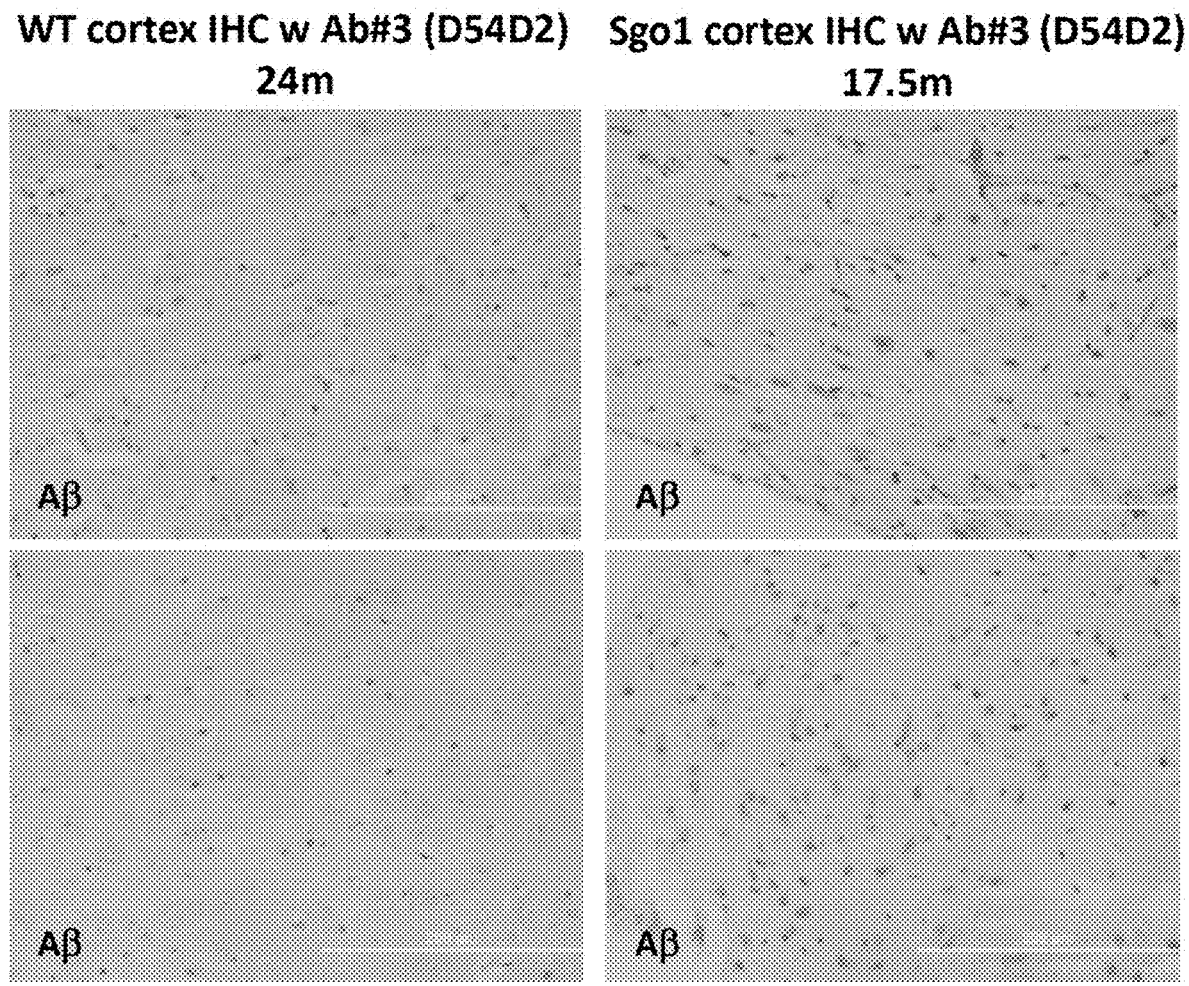
FIG. 13 shows micrographs that demonstrate that amyloid-β accumulation in Sgo1$^{-/+}$ brain cortex occurred in cell bodies. Amyloid-β IHC with D54D2 antibody for 17.5 month-old Sgo1$^{-/+}$ brain showed positive signals. However, even in 24 months of age, wild type did not show any positive signals. Bar=200 μm.
Figure 14:
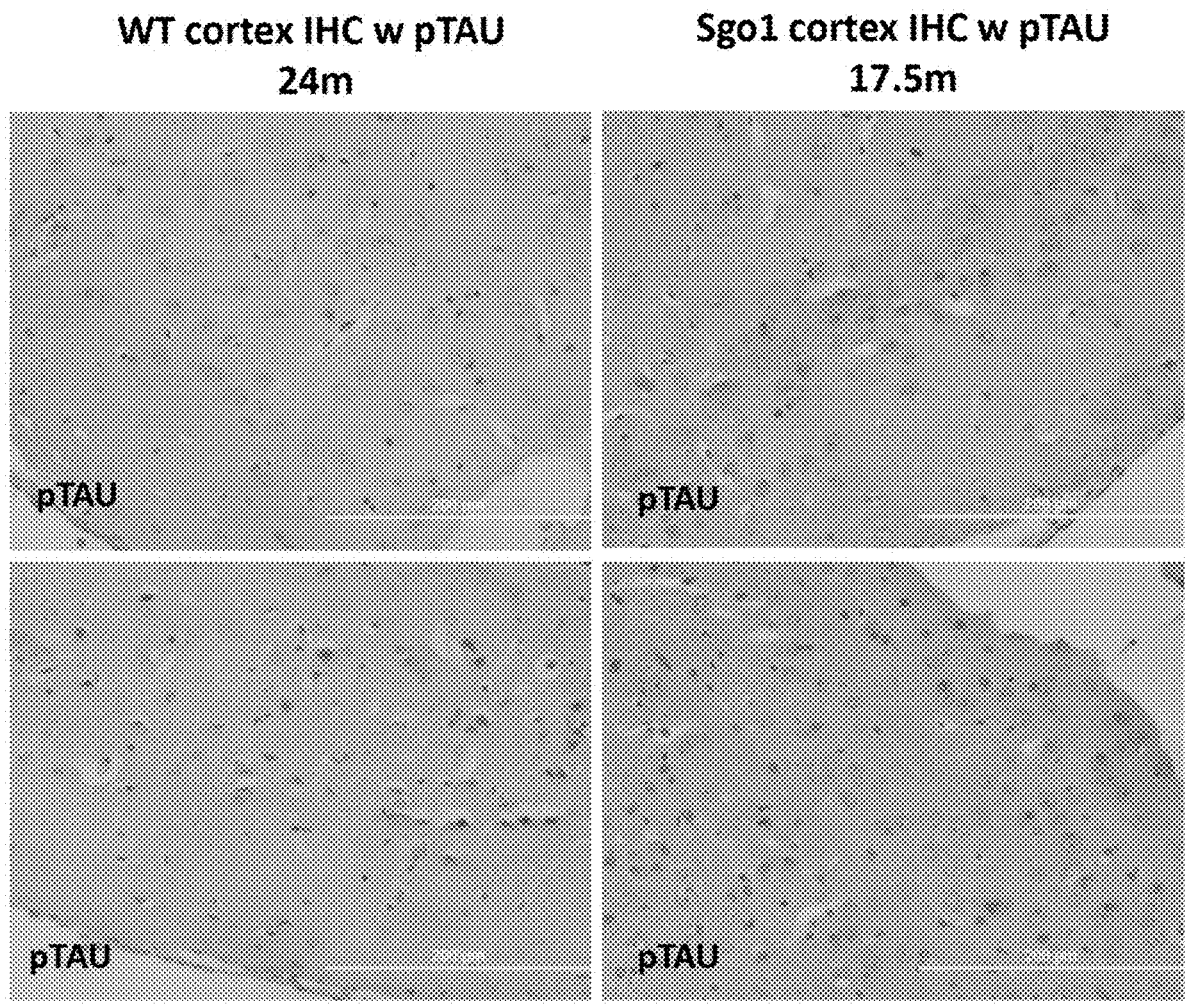
FIG. 14 shows micrographs that demonstrate p-TAU$^{S262}$ staining in 17.5 month-old Sgo1$^{-/+}$ brain. As with amyloid-β, even in 24 months of age, wild type did not show any positive staining.

Next, we investigated the timing of amyloid-beta accumulation in $Sgo1^{-/+}$ mice. In previous analysis, $Sgo1^{-/+}$ at 12 months of age did not show cerebral amyloid-beta accumulation, while $Sgo1^{-/+}$ at 24 months of age did. We tested brains from $Sgo1^{-/+}$ from different ages (12, 15, 18, and 24 months of age) with immunoblots and IHC (FIGS. 12 and 13). Immunoblots indicated that amyloid-beta p21-23 in $Sgo1^{-/+}$ was initially appearing around 15 months of age, and manifested by 18 months of age (late middle age). Expression of an aging biomarker $p21^{WAF1/CIP1}$, whose variants are also a risk factor for human AD, prematurely increased in $Sgo1^{-/+}$ in 15-18 months of age, while $p21^{WAF1/CIP1}$ expression remained low in wild type even at 24 months of age. IHC showed that amyloid-beta accumulated in cell bodies in the cortex, but not as extracellular plaques at the age. Control wild type did not show signs of amyloid-beta, even in 24 months of age. Thus, cerebral amyloid-beta accumulation in $Sgo1^{-/+}$ mice is late-onset occurring past middle age, progressive with age, and concurrent with $p21^{WAF1/CIP1}$ increase. FIG. 14 shows micrographs that demonstrate p-TAU$^{S262}$ staining in 17.5 month-old $Sgo1^{-/+}$ brain. As with amyloid-$\beta$, even in 24 months of age, wild type did not show any positive staining.

Various neuro-inflammation markers, including NFkappaB, IL1-beta, IFN-gamma, TNF-alpha, and p-MAPK, are misregulated in the brains of patients with AD (FIG. 15). Bredesen's group proposed that human AD can be categorized into three subtypes; inflammatory, non-inflammatory, and atypical. We were also interested in testing whether $Sgo1^{-/+}$-mediated amyloid-beta accumulation falls into a category as a part of model characterization.

Figure 16:
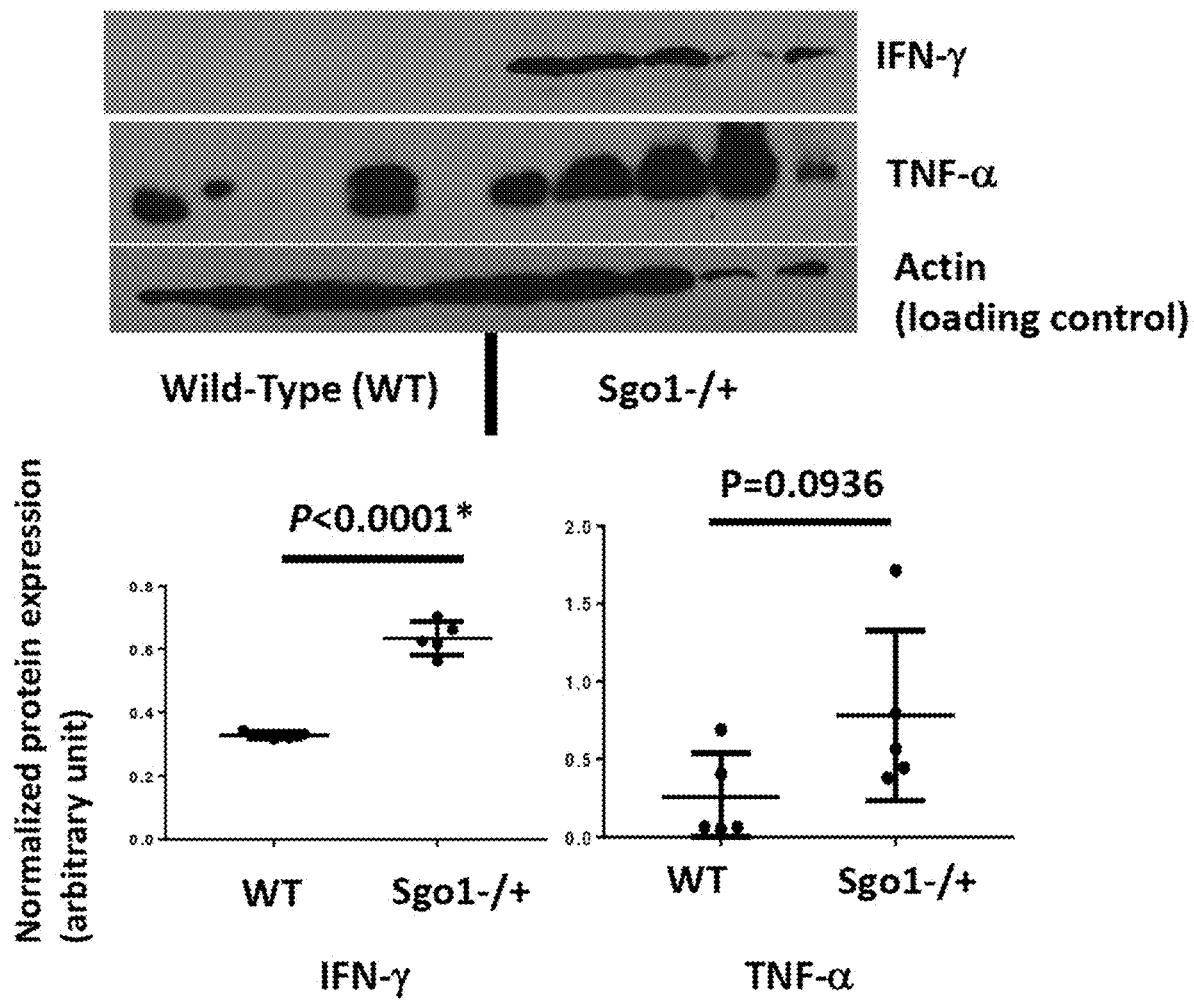
FIG. 16 shows that the AD-associated neuro-inflammation marker Interferon-gamma (IFN-γ) was upregulated in aged, amyloid-β-accumulating Sgo1$^{-/+}$ brains (P<0.0001). Another marker, TNF-alpha, was also consistently upregulated in Sgo1$^{-/+}$, showing dual presence of IFN-γ and TNF-α in Sgo1$^{-/+}$ brain. However, inconsistent expression of TNF-α in wild-type control mice led to a non-significant P-value (P=0.0936).
Figure 17:
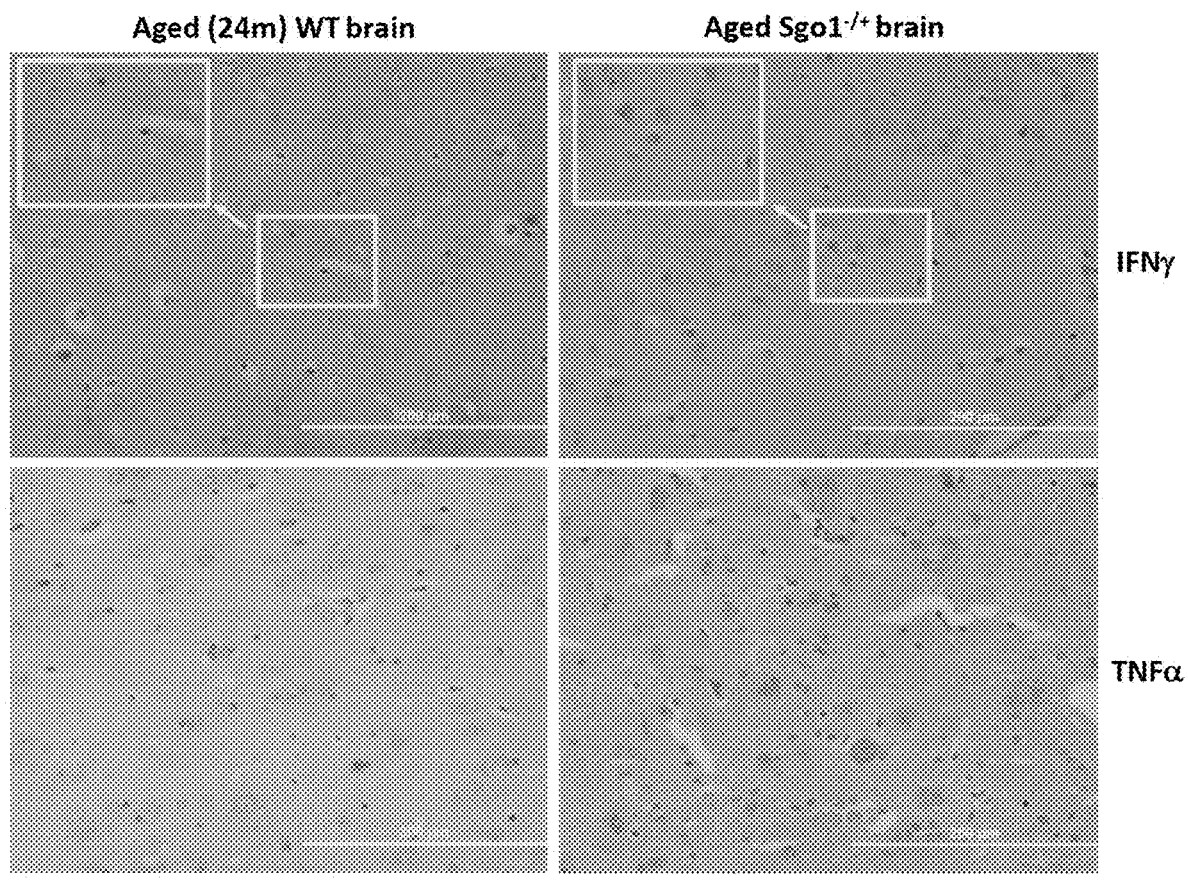
FIG. 17 shows micrographs demonstrating accumulation of IFN-γ and TNF-α in Sgo1$^{-/+}$ brain. As suggested by the immunoblots in FIG. 16, IFN-γ and TNF-α were both detected in aged Sgo1$^{-/+}$ brain. Also consistent with the immunoblots, the wild type control showed much reduced IHC signal of both IFN-γ and TNF-α.
Figure 18:
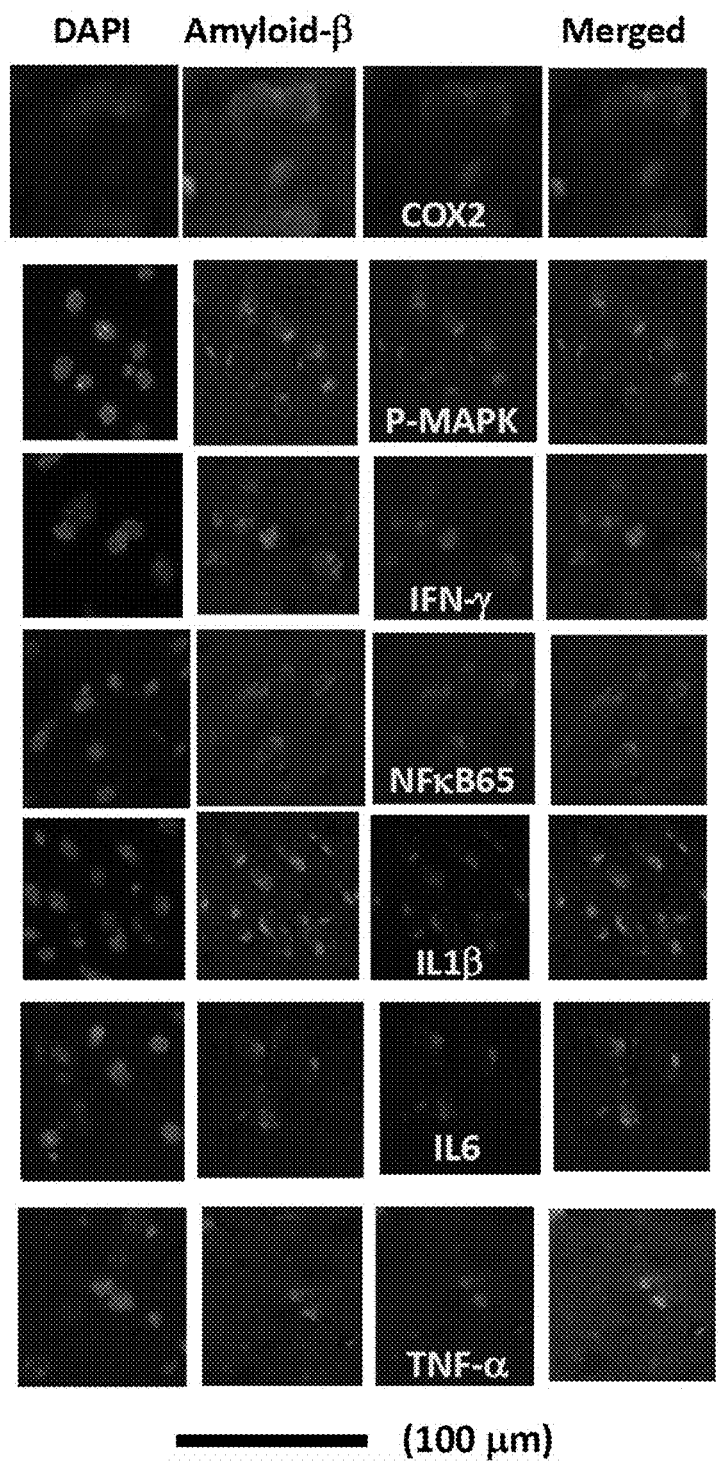
FIG. 18 shows micrographs demonstrating that amyloid-β and several neuro-inflammation markers (COX2, p-MAPK, IFN-γ, NFκB65, IL1-β, IL6, and TNF-α) co-localized in Sgo1$^{-/+}$ brain cortex cells.
Figure 19:
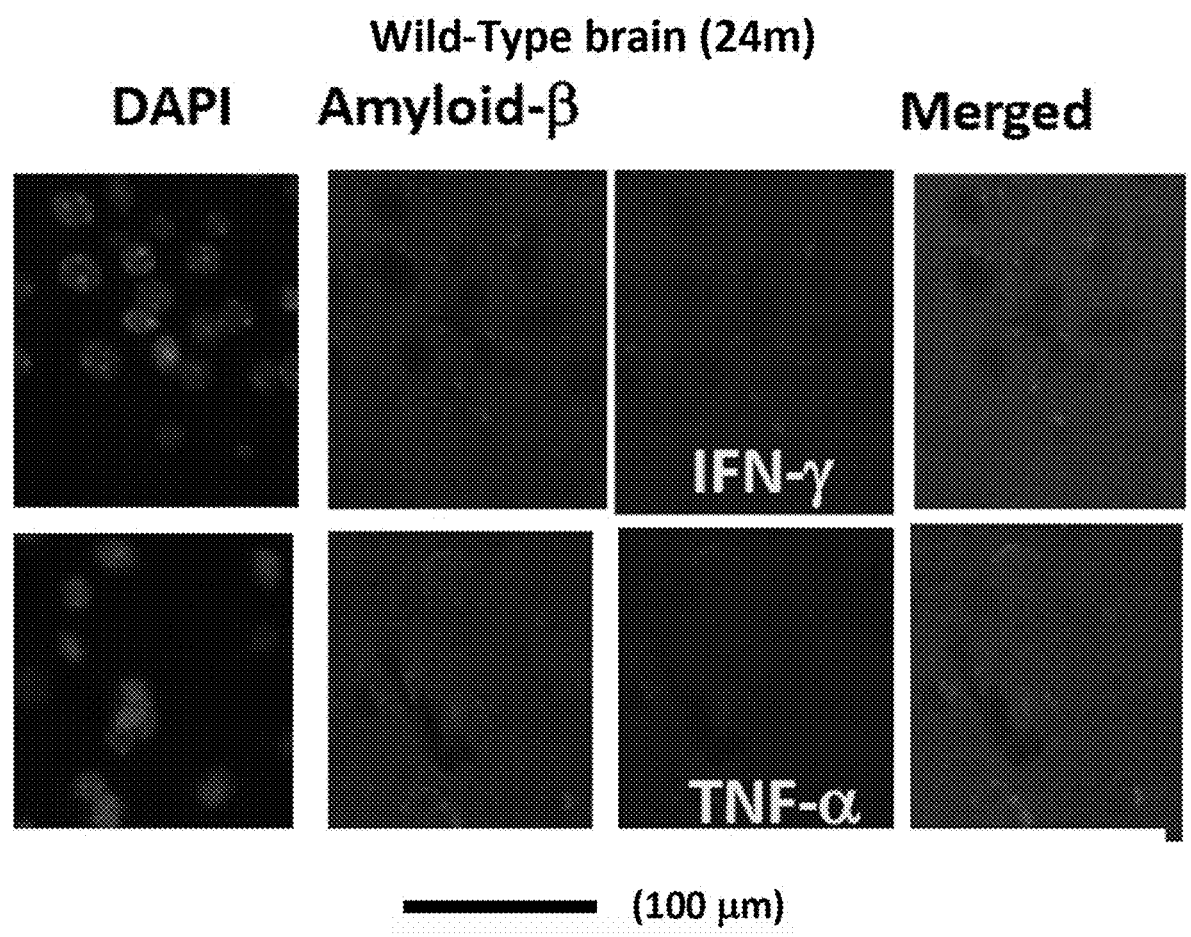
FIG. 19 shows micrographs demonstrating that age-matched wild-type mice showed little amyloid-β, and co-localization in brain cortex cells with IFN-γ and TNF-α was not observed.

First, we compared total amounts of IFN-gamma and TNF-alpha, as well as IL10, NFkappaB65, IL1-beta, and phosphor-p38MAPK. Twenty-four-month-old $Sgo1^{-/+}$ mice showed consistent expression of IFN-gamma, while age-matched wild-type mice did not express it (P<0.0001) (FIGS. 16-17). Upregulations in TNF-alpha were noted in all $Sgo1^{-/+}$ mice, indicating co-expressions of IFN-gamma and TNF-alpha in the $Sgo1^{-/+}$ model (FIG. 16). However, inconsistent expression in controls resulted in a lack of statistical significance for TNF-alpha (P=0.093) (FIG. 16). There were no significant differences in total amounts of NFkappaB65kd, IL10, IL1-beta, and phosphor-p38MAPK in control and $Sgo1^{-/+}$ mice (not shown). However, co-localization between amyloid-beta and COX2, p-MAPK, IFN-gamma, NFkappaB65kd, IL1-beta, IL6, and TNF-alpha were observed in $Sgo1^{-/+}$ mice (FIG. 18), while co-localization between amyloid-beta and p16 was not (not shown). As wild-type mice hardly express amyloid-beta, notable co-localizations in these markers were not observed in these mice (FIG. 19). The results indicated that neuro-inflammation occurs with amyloid-beta accumulation.

Figure 20:
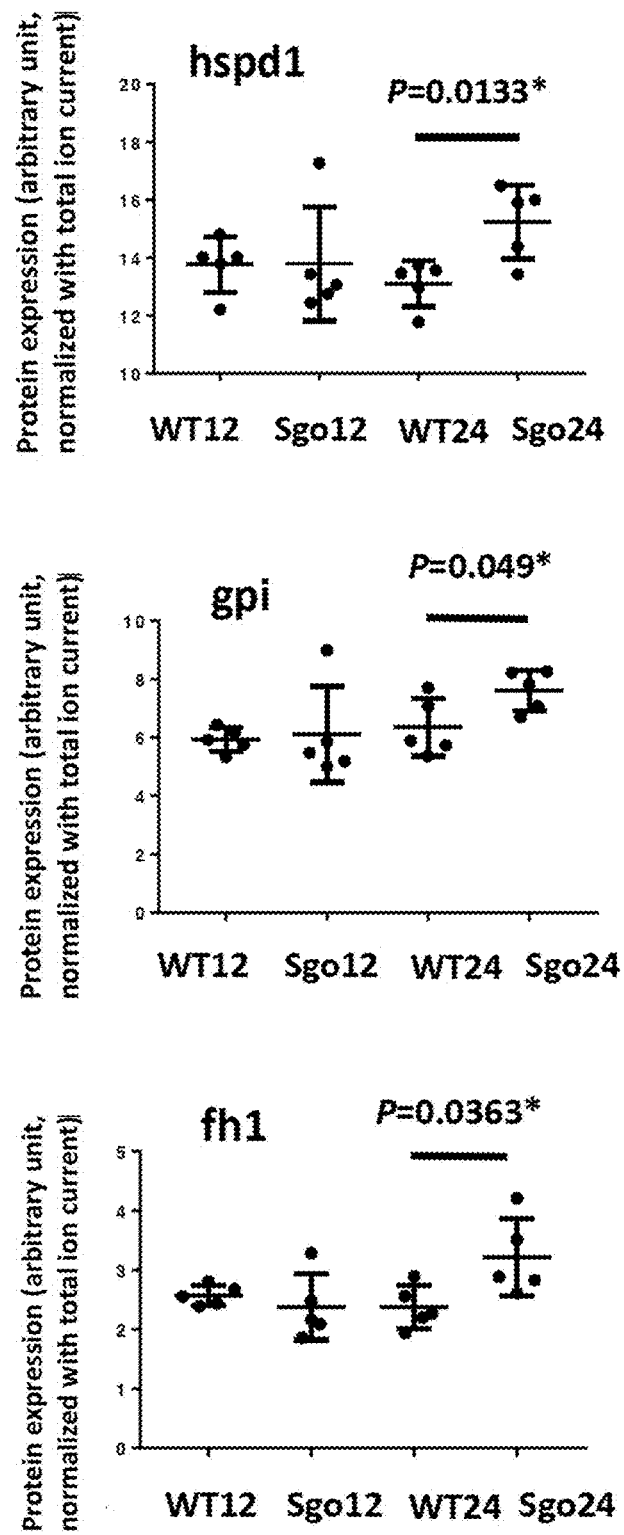
FIG. 20 shows misregulation in Sgo1$^{-/+}$ mice of several proteins (i.e., antioxidant proteins, mitochondrial energy metabolism proteins, and beta-oxidation and peroxisome proteins) relevant to human AD. Examples include proteins indicating an Sgo1$^{-/+}$-specific increase in 24-month-old brains. Hspd1 (Heat Shock Protein Family D [Hsp60] Member 1) is a mitochondrial chaperone. Gpi (Glucose-6-phosphate isomerase) and Fh1 (Fumarate Hydratase) are involved in energy generation.
Figure 21:
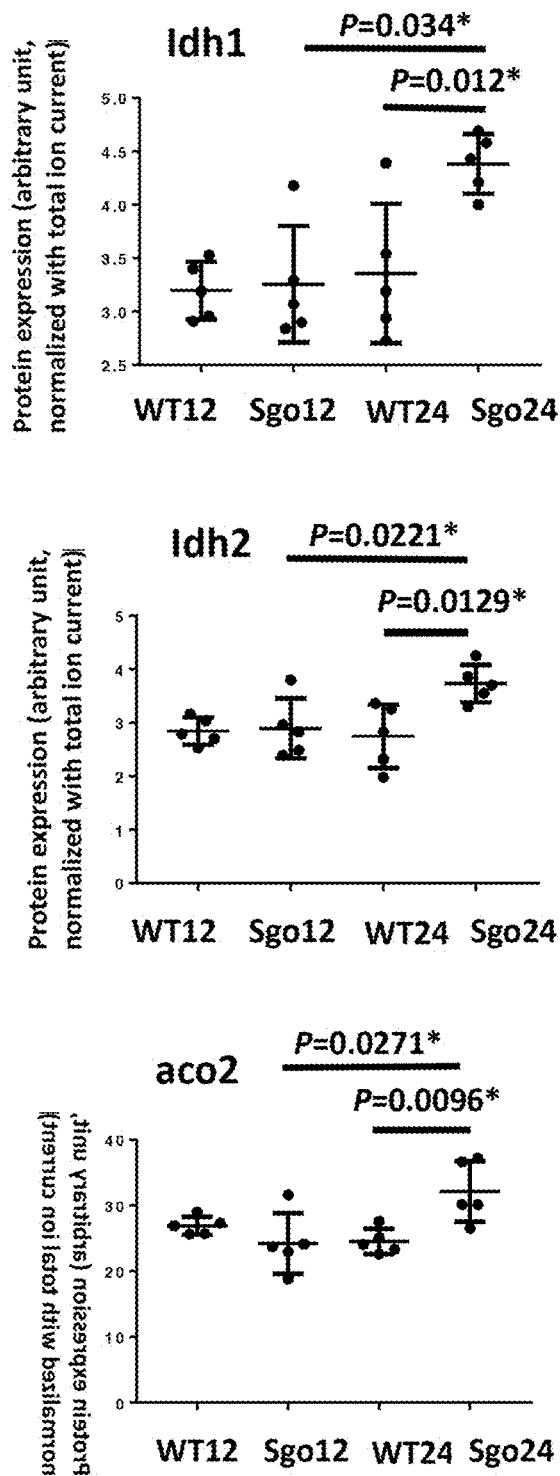
FIG. 21 shows misregulation in Sgo1$^{-/+}$ mice of several proteins (i.e., antioxidant proteins, mitochondrial energy metabolism proteins, and beta-oxidation and peroxisome proteins) relevant to human AD. Examples include proteins indicating both an Sgo1$^{-/+}$ specific increase at 24 months and age-dependent increase in Sgo1$^{-/+}$ (12-month vs. 24-month). Idh1 (Isocitrate Dehydrogenase [NADP(+)] 1, Cytosolic) and Idh2 (Isocitrate Dehydrogenase [NADP(+)] 2, Mitochondrial) are involved in energy generation. Aco2 (aconitase 2, mitochondrial) localizes in mitochondria and is a part of the TCA cycle.
Figure 22:
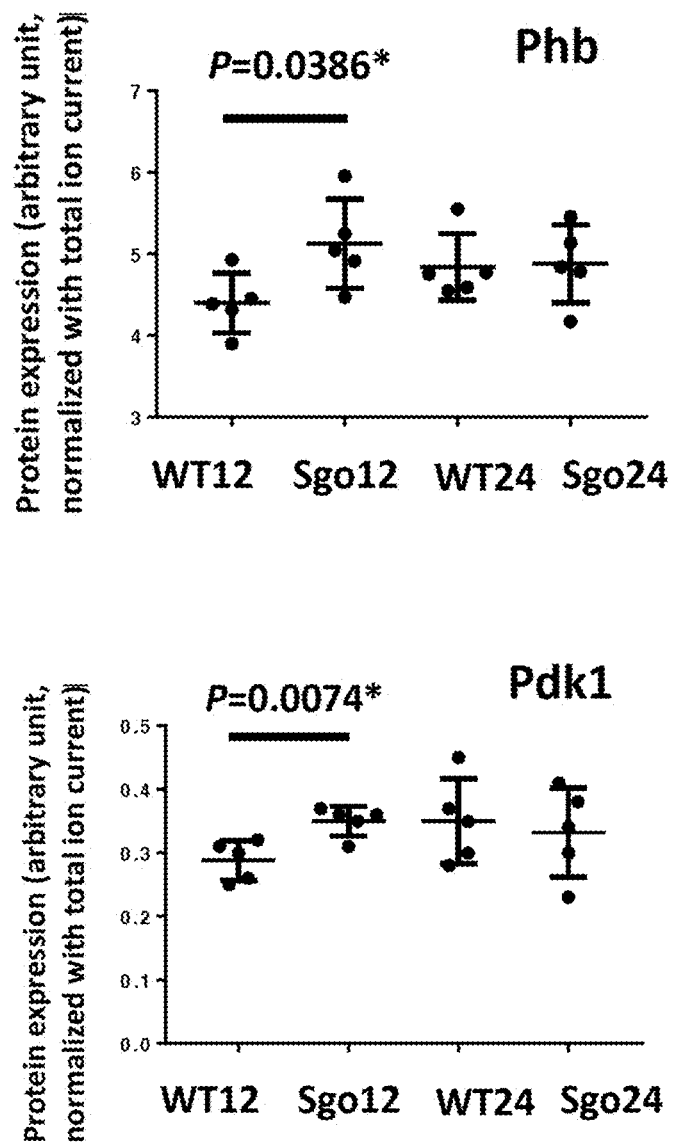
FIG. 22 shows misregulation in Sgo1$^{-/+}$ mice of several proteins relevant to human AD. Phb (Prohibitin) and Pdk1 (Phosphoinositide-dependent protein kinase 1) uniquely indicated increases in middle-aged (12-month-old) Sgo1$^{-/+}$ mice, preceding amyloid-beta accumulation at 24 months. Phb and Pdk1 are also progressively decreased in human olfactory bulb-AD proteomic analysis.
Figure 23:
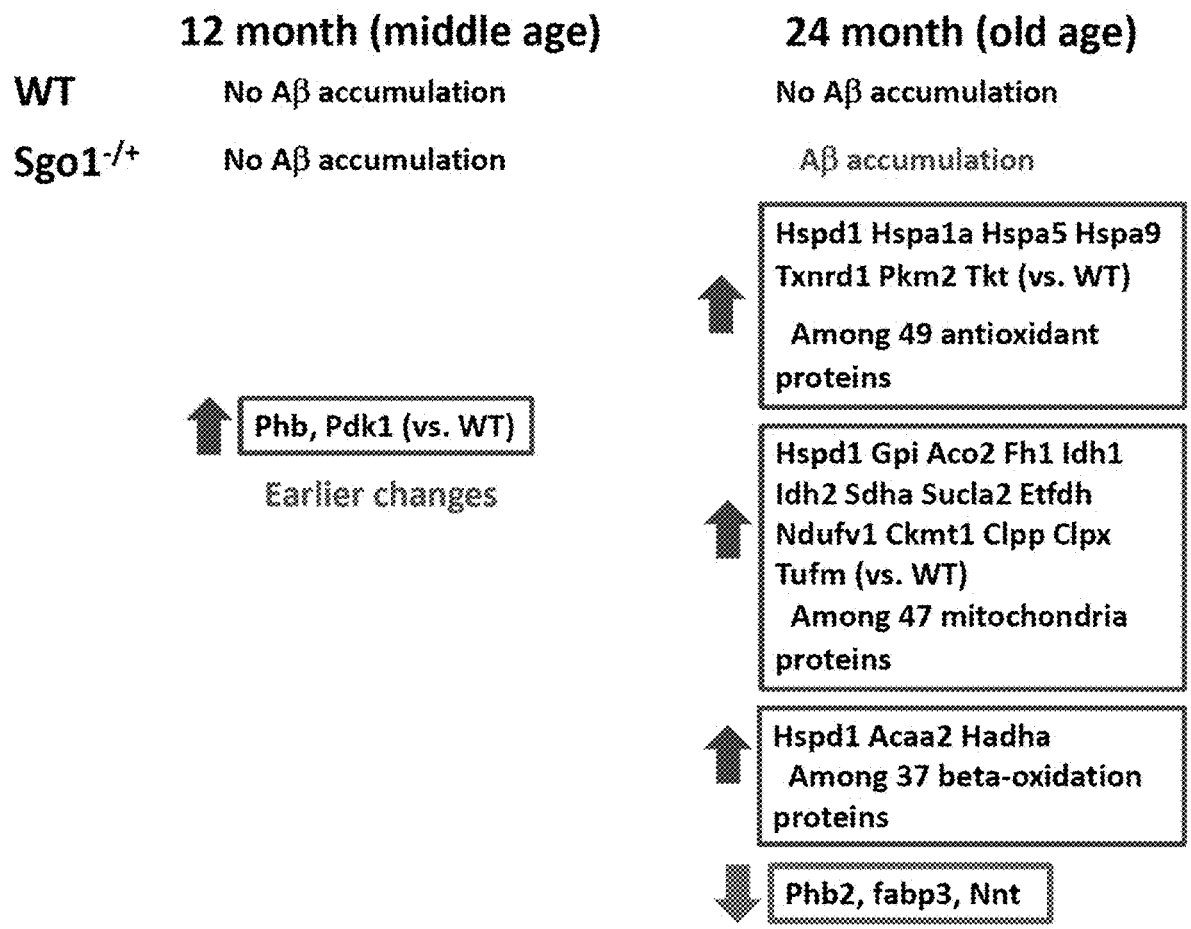
FIG. 23 is a schematic which summarizes results that the majority of protein misregulation involved increases at old age, while Phb2 (Prohibitin2), Fabp3 (Fatty Acid Binding Protein 3), and not (Nicotinamide Nucleotide Transhydrogenase) showed decreases. Many of these proteins are also misregulated in human AD.

Next, we explored other aging-associated factors as contributors to late-onset amyloid-beta accumulation in $Sgo1^{-/+}$ brains. The analyses included quantitative mass spectrometry-based protein expression panels for 49 antioxidant proteins, 47 mitochondrial energy metabolism proteins, and 37 beta-oxidation and peroxisome proteins. Not counting overlapping proteins, the analysis quantified total 130 proteins in four groups of mice (12-month-old wild-type and $Sgo1^{-/+}$, 24-month-old wild-type and $Sgo1^{-/+}$). FIG. 20 shows examples of proteins indicating an $Sgo1^{-/+}$-specific increase in 24 month-old brains. FIG. 21 shows examples of proteins indicating both an $Sgo1^{-/+}$-specific increase at 24 mo. and an age-dependent increase in $Sgo1^{-/+}$ (12 mo. vs. 24 mo.). FIG. 22 shows expression profiling for Phb (Prohibitin) and Pdk1 (Phosphoinositide-dependent protein kinase 1), which indicated an earlier increase in $Sgo1^{-/+}$ than in age-matched controls. FIG. 23 summarizes the results; the majority of misregulations were increases in 24 mo. (aged) $Sgo1^{-/+}$. Overall, 25 proteins among 130 proteins tested were misregulated in $Sgo1^{-/+}$ mice compared with wild type (FIG. 24).

Notably, increases in Phb and Pdk1 were identified in 12-month-old (middle-aged) $Sgo1^{-/+}$ mice. Progressive Phb and Pdk1 decreases were identified in olfactory bulb neuroproteomics for human patients with AD, indicating the same pathway was impacted in $Sgo1^{-/+}$ toward decreases over age. Additional proteins indicating misregulation in $Sgo1^{-/+}$ were reported as misregulated in human AD-omics analysis. For example, sporadic human AD patients showed a significant ~40-60% increase in expression levels of select genes activated by the mtUPR, including mitochondrial chaperone hspd1 and mitochondrial protease clpp, which were recapitulated in $Sgo1^{-/+}$. Perredoxin6 (prdx6) increased with human AD, which may represent an oxidative stress defense mechanism. Mitochondrial aconitase (aco2) expression in human AD with mild cognitive impairment was reported to be lower, while $Sgo1^{-/+}$ mice showed a possible compensatory increase. Oxidative inactivation of PKM2 (Pyruvate kinase isozyme M2) was proposed to be involved in the progression of AD from mild cognitive impairment. NDUFV1 (NADH:Ubiquinone Oxidoreductase Core Subunit V1) was among the critical hippocampal genes and pathways that might be involved in the pathogenesis of human AD, identified via bioinformatics. Fabp3 (fatty acid binding protein 3) is a human AD biomarker in cerebrospinal fluid and in sera. Phb2 decrease in Sgo1$^{-/+}$ may additionally contribute to cohesinopathy, as depletion of PHB2 by RNA interference caused premature sister-chromatid separation and mitotic arrest by spindle-checkpoint activation, near-identical phenotype as Sgo1 defect, indicating functional similarity of Phb2 with Sgo1 during mitosis.

The present disclosure identifies 17.5 to 18 months of age (late middle age) as the approximate age when spontaneous cerebral amyloid-beta accumulation becomes evident in the Sgo1$^{-/+}$ model. In human LOAD, cerebral amyloid-beta begins to accumulate in middle- to late-middle age, 10-15 years prior to neurofibrillary tangles and cognitive symptoms manifest. Thus, the Sgo1$^{-/+}$ model recapitulates the late-onset aspect of amyloid-beta accumulation. This identification of amyloid-beta accumulation timing helps to establish experimental condition for using the model for testing an AD drug candidate, especially for disease intervention initiated in middle age.

Among various neuro-inflammatory proteins proposed to be involved in human AD (see FIG. 15), INF-gamma and TNF-alpha were co-expressed in brain of the Sgo1$^{-/+}$ model in this work. There have been a flurry of reports suggesting involvement of INF-gamma and TNF-alpha in human AD pathology development. INF-gamma and TNF-alpha levels were higher, as well as nitric oxide production, in AD patients in mild and severe stages compared with patients in earlier phases (moderate stage and mild cognitive impairment), indicating progressive increases in INF-gamma and TNF-alpha in human AD patients. Activated TNF-alpha and the c-Jun Kinase (JNK) signaling pathway has been shown to lead to neuronal cells to cell cycle progression toward mitotic cycle, which were followed by neuronal cell death. This sequence of events is consistent with aforementioned "three-hit hypothesis". Mouse primary astrocytes treated with both INF-gamma and TNF-alpha significantly increased levels of astrocytic APP, BACE1 (an APP-Aβ conversion enzyme), and secreted Aβ40, suggesting a role of INF-gamma and TNF-alpha as priming factors for astrocytes to produce amyloid-beta. As such, from this study, targeting INF-gamma and/or TNF-alpha, and assess the effects on amyloid-beta accumulation, emerged as a next approach of interest.

Another set of results, indicating protein misregulations in Sgo1$^{-/+}$ and human AD in common pathways, also suggest the utility of Sgo1$^{-/+}$ mice as a study model for LOAD development. A critical point in interpreting the protein panel data is whether the misregulation is causal to AD, or is compensatory/antagonizing to AD development. As 24-month-old Sgo1$^{-/+}$ mice show amyloid-beta accumulation colocalizing with p-TAU, but not extensive neurofibrillary tangles or neurodegeneration, we suspect that Sgo1$^{-/+}$ represents a relatively early phase in LOAD development, and speculate that many of the misregulations are compensatory. Itemized tests and validation will be needed.

Elucidating the mechanism by which amyloid-beta starts accumulating in brains in non-symptomatic early phases would reveal effective interventions for LOAD. In the present study, we observed accumulation of amyloid-beta and its co-localization with neuro-inflammatory markers, specifically in the aged Sgo1$^{-/+}$ model mice and not in age-matched control mice. The results suggest new possible scenarios occurring at an early stage of amyloid-beta accumulation; (a) amyloid-beta accumulation during prolonged mitosis triggers inflammation markers, possibly as a part of mitotic catastrophe; alternatively, (b) cells with accumulated inflammation markers go through prolonged mitosis and accumulate amyloid-beta.

Once amyloid-beta accumulates and is released in extracellular matrix via cell death, it may become a part of feedback loop, as extracellular amyloid-beta can trigger neuro-inflammation. Although the exact sequence of events has not been determined, use of agents, such as anti-inflammatory agents (e.g., NSAIDs) and/or anti-"mitotic entry and prolongation" agents (e.g., CDK inhibitor), to decouple the events may reveal whether the agent can disrupt amyloid-beta accumulation in the model. A genetically uniform mouse model allows experimental approaches to draw biological conclusions. Yet, use of broad anti-inflammatory interventions so far has failed to benefit patients with Alzheimer's disease or mild cognitive impairment, despite benefitting mouse models of AD. Thus, stage-specific effects were hypothesized; once AD advance, modulation of inflammation alone may not suffice, and other methods (e.g., combinatorial treatment) may need to be explored.

Overall, the present findings further add to the Sgo1$^{-/+}$ model's similarities to human AD, indicating its value as an animal model of spontaneous amyloid-beta accumulation and LOAD, and supporting the model's claim to a unique niche among existing and prospective AD research models. In addition to straightforward uses for drug R&D purposes (e.g., AD drug test), various use of the model may be devised. It may be of interest to generate a set of transgenic mice with additional amyloid metabolism-related defects, such as double mutant with human APP-overexpression, with Apoe deletion, or with PSEN1 mutation.

In at least certain embodiments, the present disclosure is directed to a method of characterizing a test compound for its effect on progression of late onset Alzheimer's disease (LOAD), comprising the steps of (a) administering the test compound to a transgenic animal model for a predetermined treatment duration, wherein the transgenic animal model is (1) haploinsufficient for Shugoshin 1 (Sgo1) gene, or (2) comprises a genetic modification enabling modulation of Sgo1 expression in the brain of the animal model when exposed to an Sgo1 expression-modulating compound, (b) obtaining a sample of brain tissue from the animal model after the predetermined treatment duration, and (c) assaying the sample for at least one biomarker of Alzheimer's disease. Brain cells of the animal model may be induced to accumulate amyloid-β when exposed to the Sgo1 expression-modulating compound. The biomarker of Alzheimer's disease may selected from amyloid-β, amyloid-β/Amyloid Precursor Protein (APP) ratio, phosphorylated tau protein (p-Tau), tau protein (Tau), Activity-regulated cytoskeleton-associated protein (ARC), phospho-Histone H3 (p-H3), cyclin B, proliferating cell nuclear antigen (PCNA), glial fibrillary acidic protein (GFAP), neuronal migration protein doublecortin (DCX), pro-melanin concentrating hormone (PMCH), Gm20388, AA465934, Shisa8, Early B Cell Factor 3 (EBF3), D-amino acid oxidase (DAO), Slc6a5, PPP1r17, and Purkinje cell protein-2 (PCP2). The animal model imay be mouse. The animal model may be an Sgo1-CRISPR-cre-lox mutant strain. The Sgo1 expression-modulating compound may be tamoxifen.

In at least certain embodiments, the present disclosure is directed to an assay method for characterizing a test compound for its effect on progression of late onset Alzheimer's disease (LOAD), comprising (a) providing a test cell culture of primary brain cells cultured from an animal whose expression of Shugoshin 1 (Sgo1) gene has been genetically modified to enable modulation of Sgo1 expression in the brain of the animal when exposed to an Sgo1 expression-modulating compound, wherein the cells of the test cell culture are induced to accumulate amyloid-β due to inhibition or reduction of Sgo1 expression when the Sgo1 expression-modulating compound is added to the test cell culture, (b) treating the test cell culture with the Sgo1 expression-modulating compound and the test compound for a predetermined treatment duration, and (c) assessing the test cell culture, after the predetermined treatment duration, for the presence or amount of at least one biomarker of Alzheimer's disease and comparing said presence or amount of the at least one biomarker to that of a control cell culture treated with the Sgo1 expression-modulating compound but not treated with the test compound. The biomarker of Alzheimer's disease may selected from amyloid-β, amyloid-β/Amyloid Precursor Protein (APP) ratio, phosphorylated tau protein (p-Tau), tau protein (Tau), Activity-regulated cytoskeleton-associated protein (ARC), phospho-Histone H3 (p-H3), cyclin B, proliferating cell nuclear antigen (PCNA), glial fibrillary acidic protein (GFAP), neuronal migration protein doublecortin (DCX), pro-melanin concentrating hormone (PMCH), Gm20388, AA465934, Shisa8, Early B Cell Factor 3 (EBF3), D-amino acid oxidase (DAO), S1c6a5, PPP1r17, and Purkinje cell protein-2 (PCP2). The animal model imay be mouse. The animal model may be an Sgo1-CRISPR-cre-lox mutant strain. The Sgo1 expression-modulating compound may be tamoxifen.

In at least certain embodiments, the present disclosure is directed to an animal model for characterizing a test compound for its effect on progression of late onset Alzheimer's disease (LOAD), comprising an animal whose expression of Shugoshin 1 (Sgo1) gene has been genetically modified to enable modulation of Sgo1 expression in brain cells of the animal when exposed to an Sgo1 expression-modulating compound, wherein the brain cells of the animal are induced to accumulate amyloid-β due to inhibition or reduction of Sgo1 expression when the animal is treated with the Sgo1 expression-modulating compound. The animal model may be a mouse. The animal model may be a Sgo1-CRISPR-cre-lox mutant strain. The Sgo1 expression-modulating compound may be tamoxifen. When the animal is treated with the Sgo1 expression-modulating compound, the animal model may be further induced to produced enhanced amounts or decreased amounts of a second AD biomarker. The second AD biomarker may be selected from phosphorylated tau protein (p-Tau), tau protein (Tau), Activity-regulated cytoskeleton-associated protein (ARC), phospho-Histone H3 (p-H3), cyclin B, proliferating cell nuclear antigen (PCNA), glial fibrillary acidic protein (GFAP), neuronal migration protein doublecortin (DCX), pro-melanin concentrating hormone (PMCH), Gm20388, AA465934, Shisa8, Early B Cell Factor 3 (EBF3), D-amino acid oxidase (DAO), S1c6a5, PPP1r17, and Purkinje cell protein-2 (PCP2).

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. An in vitro method for screening a test compound for its effect on amyloid β expression comprising the steps of:
   (a) providing a cell culture of primary brain cells cultured from a mouse whose expression of Shugoshin 1 (Sgo1) gene has been genetically modified to enable modulation of Sgo1 expression in the brain of the mouse when exposed to an Sgo1 expression-modulating compound, wherein the mouse is a Sgo1-CRISPR-cre-lox mutant mouse and the Sgo1 expression-modulating compound is tamoxifen, wherein the cells of the cell culture are induced to accumulate amyloid-β due to inhibition or reduction of Sgo1 expression when the Sgo1 expression-modulating compound is added to the cell culture;
   (b) contacting the culture of (a) with a test compound and tamoxifen,
   (c) assaying the culture of (b) for the presence or amount amyloid β and comparing the culture of (b) with a control culture contacted with tamoxifen but not contacted with the test compound, wherein a reduction of amyloid β expression as compared to the control culture indicates that the test compound is effective in reducing amyloid β expression.

* * * * *